United States Patent
Wang et al.

(10) Patent No.: US 11,999,719 B2
(45) Date of Patent: *Jun. 4, 2024

(54) SOLID FORM OF COMPOUND

(71) Applicant: INXMED (NANJING) CO., LTD., Nanjing (CN)

(72) Inventors: Zaiqi Wang, Shanghai (CN); Jing Gao, Shanghai (CN); Yingxia Sang, Shanghai (CN)

(73) Assignee: INXMED (NANJING) CO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/347,335

(22) Filed: Jul. 5, 2023

(65) Prior Publication Data

US 2024/0051942 A1 Feb. 15, 2024

Related U.S. Application Data

(63) Continuation of application No. 18/019,747, filed as application No. PCT/CN2021/110069 on Aug. 2, 2021.

(30) Foreign Application Priority Data

Aug. 3, 2020 (CN) .......................... 202010768730.1
Aug. 19, 2020 (CN) .......................... 202010837005.5

(51) Int. Cl.
*C07D 401/14* (2006.01)

(52) U.S. Cl.
CPC ........ *C07D 401/14* (2013.01); *C07B 2200/13* (2013.01)

(58) Field of Classification Search
CPC .......................... C07D 401/14; C07B 2200/13
USPC ........................................................ 514/272
See application file for complete search history.

(56) References Cited

U.S. PATENT DOCUMENTS 8,846,689 B2 9/2014 Stadtmueller et al.

FOREIGN PATENT DOCUMENTS

| CN | 104478865 A | 4/2015 | | |
|---|---|---|---|---|
| WO | 2010058032 A2 | 5/2010 | | |
| WO | WO-2010058032 A2 * | 5/2010 | ........... | A61K 31/506 |
| WO | 2020202005 A1 | 10/2020 | | |
| WO | WO-2020191448 A1 * | 10/2020 | ............. | A61P 35/00 |
| WO | 2021098679 A1 | 5/2021 | | |
| WO | 2021104454 A1 | 6/2021 | | |
| WO | 2021154929 A1 | 8/2021 | | |
| WO | 2021155764 A1 | 8/2021 | | |

OTHER PUBLICATIONS

Dagogo-Jack, Nature Reviews Clinical Oncology, vol. 15, p. 81-94 (2018), published online Nov. 8, 2017, Abstract, p. 81 (Year: 2018).*
De Jonge et al., Targeted Oncology (2019) 14:43-55, "Phase I Study of BI 853520, an Inhibitor of Focal Adhesion Kinase, in Patients with Advanced or Metastatic Nonhematologic Malignancies" (Year: 2019).*
Mohanty et al. Expert Opinion on Investigational Drugs, 2020, 29:4, 399-409. "FAK-targeted and combination therapies for the treatment of cancer: an overview of phase I and II clinical trials". (Year: 2020).*
Laszlo et al., "The FAK Inhibitor BI 853520 inhibits spherois formation and orthotopic tumor growth in malignant pleural mesothelioma," J Mol Med (2018) vol. 97, pp. 231-242.
International Search Report and Written Opinion issued in PCT/CN2021/110069 mailed Nov. 4, 2021.
Hirt et al., "BI 853520, a potent and highly selective inhibitor of protein tyrosine kinase 2 (focal adhesion kinase), shows efficacy in multiple xenograft models of human cancer," Mol Cancer Ther (2011) vol. 10, Supp. 11, Abstract A249.
Hirt et al., "Efficacy of the highly selective focal adhesion kinase inhibitor BI 853520 in adenocarcinoma xenograft models is linked to a mesenchymal tumor phenotype," Oncogenesis (2018) vol. 7, Article 21, 11 pages.
Oktay et al., "Focal Adhesion Kinase as a Marker of Malignant Phenotype in Brest and Cerviccal Carcinomas," Hum Pathol (2003) vol. 34, pp. 240-245.

* cited by examiner

*Primary Examiner* — Jared Barsky
*Assistant Examiner* — Liyuan Mou
(74) *Attorney, Agent, or Firm* — K&L Gates LLP

(57) ABSTRACT

Provided is a solid form of a compound of formula (I) or a salt thereof, or a solvate thereof, or a solvate of a salt thereof, or a mixture thereof.

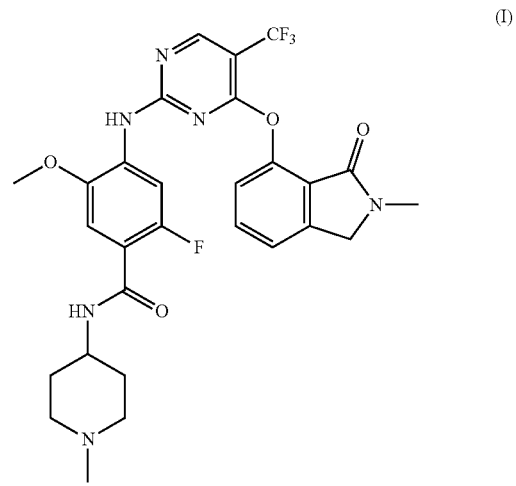

12 Claims, 15 Drawing Sheets

SOLID FORM OF COMPOUND

FIELD OF THE INVENTION

The present disclosure belongs to the field of medicinal chemistry. In particular, the present disclosure relates to a solid form of a compound.

BACKGROUND OF THE INVENTION

FAK, also known as protein tyrosine kinase 2 (PTK2), is a non-receptor tyrosine kinase and a key component of the focal adhesion complex. FAK plays a critical role in mediating integrin and growth factor signaling to regulate tumor cell invasion, proliferation and survival. FAK is widely expressed and evolutionarily conserved. Studies in the past two decades have shown that FAK is overexpressed in a variety of solid tumors, and the expression level is negatively correlated with tumor prognosis. Recent studies have also shown that FAK plays an important role in regulating the tumor microenvironment, suggesting that FAK plays an important role in adaptive drug resistance of immunotherapy and anti-tumor therapy.

The compound of formula (I) is a FAK inhibitor, which exhibits anti-tumor activity in CDX (cell-line-derived xenograft) models of various tumors. For the preparation of the desired drug substance, we urgently need to find a solid form that improves the druggability of the compound, especially has beneficial properties in terms of crystallinity, stability, hygroscopicity, and solubility.

SUMMARY OF THE INVENTION

In one aspect, the present disclosure provides a solid form of a compound of formula (I) or a salt thereof, or a solvate thereof, or a solvate of a salt thereof, or a mixture thereof:

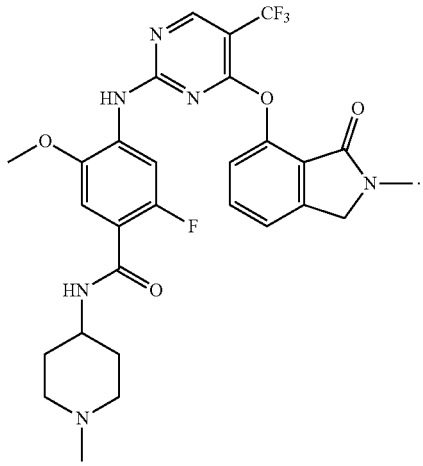

(I)

Optionally, the salt is a pharmaceutically acceptable salt.
Optionally, the solid form is a crystalline form.
Optionally, the solid form is free base of the compound of formula (I).
Optionally, the solid form is crystalline form A of the free base of the compound of formula (I).
Optionally, it has X-ray powder diffraction (XRPD) including peaks at 10.979, 19.26, 21.581 and 24.801 degrees 2θ.

Optionally, it has X-ray powder diffraction (XRPD) including peaks at 4.781, 10.979, 19.26, 21.581, 22.26 and 24.801 degrees 2θ.

Optionally, it has X-ray powder diffraction (XRPD) including peaks at 4.781, 9.58, 10.979, 11.459, 14.678, 17.402, 19.26, 21.581, 22.26, 22.54, 24.801 and 29.219 degrees 2θ.

Optionally, it has X-ray powder diffraction (XRPD) including peaks at 4.781, 7.361, 7.619, 9.58, 10.54, 10.979, 11.459, 12.34, 12.96, 13.278, 14.678, 17.402, 18.54, 19.26, 19.918, 21.581, 22.26, 22.54, 23.521, 24.217, 24.801, 25.181, and 29.219 degrees 2θ.

Optionally, it has X-ray powder diffraction (XRPD) including peaks at one or more of 4.781, 5.255, 6.395, 7.361, 7.619, 8.818, 9.58, 10.54, 10.979, 11.459, 12.34, 12.96, 13.278, 14.678, 15.58, 16.377, 17.402, 18.54, 19.26, 19.918, 20.819, 21.581, 22.26, 22.54, 23.22, 23.521, 24.217, 24.801, 25.181, 26.101, 26.439, 27.38, 28.543, 29.219, 29.721, 31.4, 31.717, 32.621, 33.118, 33.118, 33.458, 34.462, 35.178, 35.658, 36.556, 36.999, 39.335, 39.836, 43.02, and 44.279. Optionally, it has an XRPD pattern substantially as shown in FIG. 1.

Optionally, it exhibits an endothermic event as characterized by DSC, with an onset temperature at about 212.95° C. and/or a peak temperature at about 214.24° C.

Optionally, the solid form is crystalline form I of tartrate salt of formula (I).

Optionally, it has X-ray powder diffraction (XRPD) including peaks at 10.34, 17.981, 18.281 and 21.901 degrees 2θ.

Optionally, it has X-ray powder diffraction (XRPD) including peaks at 4.627, 10.34, 17.981, 18.281, 21.901 and 23.121 degrees 2θ.

Optionally, it has X-ray powder diffraction (XRPD) including peaks at 4.627, 10.34, 13.019, 17.981, 18.281, 21.2, 21.901, 23.121, 27.299, 27.541 and 29.879 degrees 2θ.

Optionally, it has X-ray powder diffraction (XRPD) including peaks at 4.627, 10.34, 13.019, 15.76, 16.54, 17.159, 17.981, 18.281, 20.538, 21.2, 21.901, 23.121, 24.721, 25.659, 27.299, 27.541, 29.879, 32.277 and 41.821 degrees 2θ.

Optionally, it has X-ray powder diffraction (XRPD) including peaks at one or more of 4.637, 9.143, 10.34, 11.56, 13.019, 13.7, 14.039, 14.838, 15.76, 16.54, 17.159, 17.981, 18.281, 19.14, 19.795, 20.538, 21.2, 21.901, 23.121, 23.879, 24.721, 25.659, 26.179, 27.299, 27.541, 28.22, 29.879, 30.459, 31.723, 32.277, 33.479, 33.941, 34.802, 35.401, 36.234, 36.536, 37, 37.666, 38.296, 38.777, 39.602, 39.94, 40.877, 41.821, 42.981, and 44.403.

Optionally, it has an XRPD pattern substantially as shown in FIG. 3.

Optionally, it exhibits an endothermic event as characterized by DSC, with an onset temperature at about 235.42° C. and/or a peak temperature at about 235.89° C.

Optionally, the solid form is crystalline form III of tartrate salt of formula (I).

Optionally, it has X-ray powder diffraction (XRPD) including peaks at 13.2, 13.519, 15.181, 21.901, 22.521, 23.121 and 24.9 degrees 2θ.

Optionally, it has X-ray powder diffraction (XRPD) including peaks at 13.2, 13.519, 15.181, 18.539, 21.901, 22.521, 23.121, 23.219, 24.9, 26.419 and 26.62 degrees 2θ.

Optionally, it has X-ray powder diffraction (XRPD) including peaks at 8.939, 11.199, 13.2, 13.519, 14.02, 15.181, 18.539, 20.921, 21.901, 22.521, 23.121, 23.219, 24.9, 26.419 and 26.62 degrees 2θ.

Optionally, it has X-ray powder diffraction (XRPD) including peaks at one or more of 6.159, 7.339, 8.939, 10.179, 11.199, 11.481, 13.2, 13.519, 14.02, 14.719, 15.181, 16.461, 17.64, 17.999, 18.539, 19.22, 19.479, 20.019, 20.442, 20.921, 21.619, 22.521, 23.219, 23.518, 24.019, 24.9, 25.281, 25.9, 26.419, 26.62, 28.198, 28.978, 28.978, 29.703, 30.779, 31.202, 32.357, 33.117, 33.819, 34.183, 35.116, 36.059, 36.519, 37.219, 38.061, 39.161, 40.659, 41.654, 41.903, and 43.139.

Optionally, it has an XRPD pattern substantially as shown in FIG. 5.

Optionally, it exhibits an endothermic event as characterized by DSC, with an onset temperature at about 235.42° C. and/or a peak temperature at about 235.89° C.

Optionally, it is phosphate salt of the compound of formula (I).

Optionally, it is crystalline form I of the phosphate salt of the compound of formula (I).

Optionally, it has X-ray powder diffraction (XRPD) including peaks at 13.76, 19.08, 20.581 and 22.319 degrees 2θ.

Optionally, it has X-ray powder diffraction (XRPD) including peaks at 13.76, 15.941, 19.08, 20.581, 22.319 and 24.642 degrees 2θ.

Optionally, it has X-ray powder diffraction (XRPD) including peaks at 13.76, 14.52, 15.941, 19.08, 20.581, 22.319, 23.381, 23.818, 24.642 and 28.219 degrees 2θ.

Optionally, it has X-ray powder diffraction (XRPD) including peaks at 9.121, 10.082, 12.6, 13.76, 14.52, 15.941, 18.581, 19.08, 19.781, 20.581, 22.319, 23.381, 23.818, 24.642, 25.66, 26.537, 28.219, 29.419 and 33.98 degrees 2θ.

Optionally, it has an XRPD pattern substantially as shown in FIG. 10.

Optionally, it is maleate salt of the compound of formula (I).

Optionally, it is crystalline form I of the maleate salt of the compound of formula (I).

Optionally, it has X-ray powder diffraction (XRPD) including peaks at 18.459, 20.237, 22.185 and 24.12 degrees 2θ.

Optionally, it has X-ray powder diffraction (XRPD) including peaks at 10.32, 15.998, 18.459, 20.237, 22.185 and 24.12 degrees 2θ.

Optionally, it has X-ray powder diffraction (XRPD) including peaks at 6.801, 10.32, 15.998, 18.459, 19.761, 20.237, 22.185, 24.12, 25.599 and 35.258 degrees 2θ.

Optionally, it has X-ray powder diffraction (XRPD) including peaks at 6.801, 9.575, 10.32, 13.258, 13.662, 15.041, 15.998, 18.459, 19.761, 20.237, 20.781, 21.498, 21.78, 22.185, 24.12, 25.599, 27.062, 28.203 and 35.258 degrees 2θ.

Optionally, it has an XRPD pattern substantially as shown in FIG. 12.

Optionally, it is benzoate salt of the compound of formula (I).

Optionally, it is crystalline form I of the benzoate salt of the compound of formula (I).

Optionally, it has X-ray powder diffraction (XRPD) including peaks at 6.639, 8.461, 20.16 and 21.699 degrees 2θ.

Optionally, it has X-ray powder diffraction (XRPD) including peaks at 6.639, 8.461, 12.119, 14.52, 20.16 and 21.699 degrees 2θ.

Optionally, it has X-ray powder diffraction (XRPD) including peaks at 3.981, 6.639, 8.461, 12.119, 14.52, 15.441, 20.16, 20.639, 21.699 and 24.659 degrees 2θ.

Optionally, it has X-ray powder diffraction (XRPD) including peaks at 3.981, 6.639, 8.461, 9.6, 12.119, 12.602, 14.52, 15.441, 16.882, 18.12, 18.941, 20.16, 20.639, 21.699, 23.378, 23.719, 24.659, 28.418 and 29.259 degrees 2θ.

Optionally, it has an XRPD pattern substantially as shown in FIG. 18.

In another aspect, the present disclosure provides tartrate salt of a compound of formula (I),

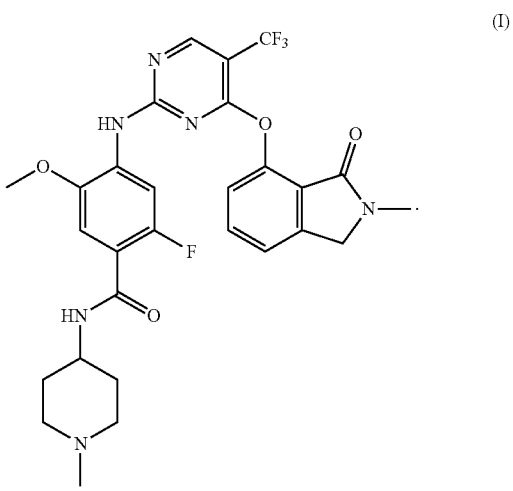

Optionally, it is crystalline form I of the tartrate salt of the compound of formula (I).

Optionally, it has X-ray powder diffraction (XRPD) including peaks at 10.34, 17.981, 18.281 and 21.901 degrees 2θ.

Optionally, it has X-ray powder diffraction (XRPD) including peaks at 4.627, 10.34, 17.981, 18.281, 21.901 and 23.121 degrees 2θ.

Optionally, it has X-ray powder diffraction (XRPD) including peaks at 4.627, 10.34, 13.019, 17.981, 18.281, 21.2, 21.901, 23.121, 27.299, 27.541 and 29.879 degrees 2θ.

Optionally, it has X-ray powder diffraction (XRPD) including peaks at 4.627, 10.34, 13.019, 15.76, 16.54, 17.159, 17.981, 18.281, 20.538, 21.2, 21.901, 23.121, 24.721, 25.659, 27.299, 27.541, 29.879, 32.277 and 41.821 degrees 2θ.

Optionally, it has X-ray powder diffraction (XRPD) including peaks at one or more of 4.637, 9.143, 10.34, 11.56, 13.019, 13.7, 14.039, 14.838, 15.76, 16.54, 17.159, 17.981, 18.281, 19.14, 19.795, 20.538, 21.2, 21.901, 23.121, 23.879, 24.721, 25.659, 26.179, 27.299, 27.541, 28.22, 29.879, 30.459, 31.723, 32.277, 33.479, 33.941, 34.802, 35.401, 36.234, 36.536, 37, 37.666, 38.296, 38.777, 39.602, 39.94, 40.877, 41.821, 42.981, 44.403.

Optionally, it has an XRPD pattern substantially as shown in FIG. 3.

In another aspect, the present disclosure provides a method for preparing a solid form of a compound of formula (I), comprising steps of:

exposing a non-solid form of the compound of formula (I) to one or more solvents, dissolving the non-solid form of the compound of formula (I) by stirring under heating condition for a period of time, and then cooling to room temperature to obtain a solid form, wherein the compound of formula (I) is

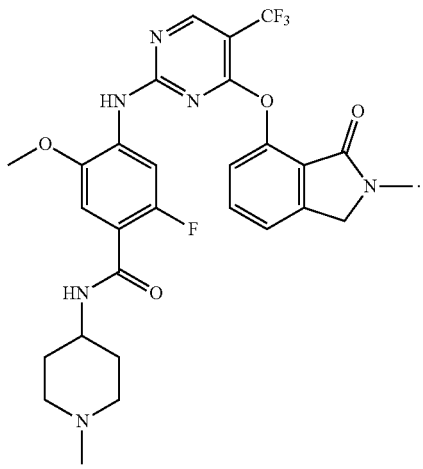

Optionally, the solvent is absolute ethanol.

In another aspect, the present disclosure provides a method for preparing a solid form of a salt of a compound of formula (I), comprising steps of:

exposing a non-solid form of the compound of formula (I) and an acid radical to one or more solvents, dissolving the non-solid form of the compound of formula (I) and the acid radical by stirring under heating condition for a period of time, and then cooling to room temperature to obtain a solid form of the salt of the compound of formula (I), wherein the compound of formula (I) is

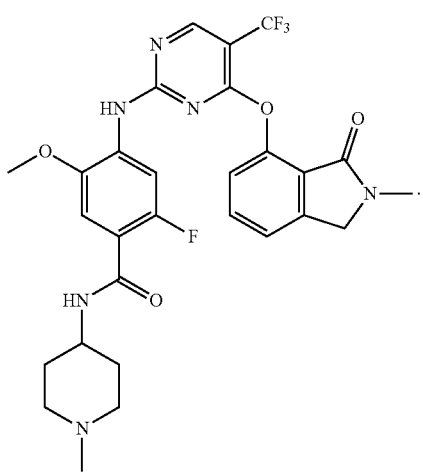

In another aspect, the present disclosure provides a pharmaceutical composition, characterized in that the pharmaceutical composition comprises the solid form of the compound of formula (I) described in the present disclosure, in particular, an effective amount of the solid form of the compound of formula (I) described in the present disclosure, and a pharmaceutically acceptable excipient.

In another aspect, the present disclosure provides a use of the solid form of the compound of formula (I) or the pharmaceutical composition described in the present disclosure as a FAK inhibitor.

In another aspect, the present disclosure provides a use of the solid form of the compound of formula (I) or the pharmaceutical composition described in the present disclosure in the manufacture of a medicament for the treatment of Hodgkin's lymphoma, non-Hodgkin's lymphoma, lung cancer, liver cancer, bile duct cancer, myelodysplastic syndrome, leukemia, thyroid cancer, glioma, colon cancer, rectal cancer, colorectal cancer, ovarian cancer, bladder cancer, prostate cancer, breast cancer, sarcoma, neuroblastoma, renal cell carcinoma, head and neck cancer, gastric cancer, esophageal cancer, gastroesophageal junction cancer, thymus cancer, pancreatic cancer, uterine cancer, testicular cancer, melanoma, skin cancer, mesothelioma, thymoma, germinoma, glioblastoma, nasopharyngeal cancer, oropharyngeal cancer, or laryngeal cancer; especially non-small cell lung cancer, small cell lung cancer, colorectal cancer, pancreatic cancer, leukemia, bladder cancer, cervical cancer, bile duct cancer, esophageal cancer, gastric cancer, glioblastoma, liver cancer, melanoma, mesothelioma, ovarian cancer, prostate cancer, kidney cancer, sarcoma, thyroid cancer, testicular cancer, thymoma, or uterine cancer.

DETAILED DESCRIPTION OF THE INVENTION

Figure 1:
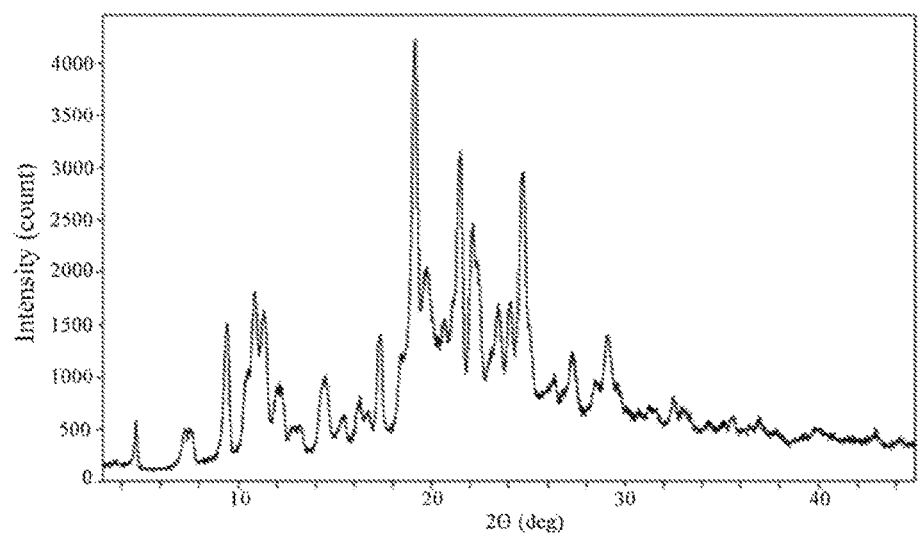
FIG. 1 is the X-ray powder diffraction (XRPD) pattern of crystalline form A of free base of the compound of formula (I).

The following examples are provided to further illustrate the present disclosure. It should be understood that these examples are used only to illustrate the present disclosure, but not to limit the scope of the present disclosure.

The experimental methods without specific conditions indicated in the following examples can be carried out according to conventional conditions of this type of reaction or according to conditions suggested by the manufacturer.

The experimental materials and reagents used in the following examples can be obtained from commercially available channels unless specified otherwise.

Unless defined otherwise, all technical and scientific terms used herein have the same meanings as commonly understood by those skilled in the art.

As used herein, the term "about" or "approximately" when used in combination with a value or range of values means that it may deviate from the described value or range of values by a reasonable range considered by those skilled in the art, for example within experimental variation (or within statistics experimental error), so it may vary, for example, between 1% and 15%, between 1% and 10%, between 1% and 5%, between 0.5% and 5%, or between 0.5% and 1% of the described value or range of values. The situation where a value or range of values is preceded by the term "about" also includes an embodiment of the given value. For example, "about 3° C." discloses an embodiment where the temperature is "3° C." Throughout this specification, the terms "about" and "approximately" are used entirely interchangeably. The term "between" includes endpoint numbers at both ends of the range limit. For example, "between 3 and 5" describes a range that includes the numbers "3" and "5." As used herein, a wave line (i.e., "~") preceding a value or range of values means "about" or "approximately."

As used herein, the term "mixing" refers to forming a mixture of one or more chemical entities with another chemical entity or entities. Mixing includes the process of adding one or more compounds to a solid, liquid or gas mixture, or liquid solution, or multiphase liquid mixture of one or more compounds (the same or other chemical entities), e.g., bond formation or cleavage; salt formation, solvate formation, chelation, or other association that changes non-bonds. The effect of mixing may involve altering one or more compounds, such as by isomerization (e.g., interconversion, resolution of one isomer from another, or racemization).

As used herein, the term "pharmaceutically acceptable" means non-toxic, biologically tolerable, and suitable for administration to a subject.

As used herein, the term "pharmaceutically acceptable salt" refers to a non-toxic, biologically tolerable salt suitable for administration to a subject. A pharmaceutically acceptable salt of the compound refers to a non-toxic, biologically tolerable acid addition salt suitable for administration to a subject, including but not limited to: acid addition salts of said compound with an inorganic acid such as hydrochloride, hydrobromide, carbonate, bicarbonate, phosphate, sulfate, sulfite, nitrate, etc.; and acid addition salts of said compound with an organic acids, such as formate, acetate, malate, maleate, fumarate, tartrate, succinate, citrate, lactate, mesylate, p-toluenesulfonate, 2-hydroxyethanesulfonate, benzoate, salicylate, stearate and salts with an alkanedicarboxylic acid of formula $HOOC-(CH_2)_n-COOH$ (wherein n is 0-4), and the like. In addition, if a compound of the present disclosure is obtained as an acid addition salt, the free base can be obtained by basifying a solution of the salt. Conversely, if the product is a free base, a pharmaceutically acceptable salt can be prepared by dissolving the free base in a suitable organic solvent and treating the solution with an acid by conventional methods of preparing acid addition salts from free base compounds. Those skilled in the art will recognize various synthetic methods that can be used to prepare pharmaceutically acceptable salts. In some embodiments, the salt is tartrate, hydrochloride, succinate, salicylate or fumarate. In some embodiments, the salt is tartrate.

As used herein, the term "solvate" refers to a compound that further includes a stoichiometric or non-stoichiometric solvent bound by a non-covalent intermolecular force. For example, a solvate is a "hydrate" when the solvent is water. A solvate may be a channel solvate. It should be understood that the term "solvate" as used herein includes a compound and a solvate of a compound, as well as a mixture thereof.

Unless specified otherwise, each of the terms "solvent", "organic solvent" and "inert solvent" as used herein refers to an organic solvent that is inert under the described reaction condition, including but not limited to benzene, toluene, acetonitrile (MeCN), ethyl acetate (EtOAc), isopropyl acetate (IPAc), hexane, heptane, dioxane, tetrahydrofuran (THF), dimethylformamide (DMF), chloroform, dichloromethane (DCM), diethyl ether, methanol (MeOH), ethanol, isopropanol, butanol, methyl tert-butyl ether (MTBE or TBME), dioxane, acetone, 2-butanone (MEK), N-methylpyrrolidone (NMP), pyridine, etc. In some embodiments, the terms "solvent", "organic solvent" and "inert solvent" as used herein include but are not limited to ethyl acetate (EtOAc), tetrahydrofuran (THF), methanol (MeOH), 75% ethanol, dioxane, methyl tert-butyl ether, acetone, and the like. Unless specified to the contrary, the solvents used in the reactions described herein are inert organic solvents.

The term "subject" as used herein refers to both mammals and non-mammals. Mammal means any member of the class Mammalia, which includes, but is not limited to: humans; non-human primates such as chimpanzees and other apes and monkey species; farm animals such as cattle, horses, sheep, goats and pigs; domestic animals such as rabbits, dogs and cats; laboratory animals including rodents such as rats, mice and guinea pigs; etc. Examples of non-mammals include, but are not limited to, birds and the like. The term "subject" is not limited to a specific age or gender. In some embodiments, the subject is a human.

The term "treating" as used herein refers to obtaining a desired pharmacological and/or physiological effect. The effect may be therapeutic, including partial or substantial achievement of one or more of the following results: partial or total alleviation of the extent of the disease, condition or syndrome; improvement of clinical symptoms or indicators associated with the disease; or delay, suppression or reduction of likelihood of disease, condition or syndrome progression.

The term "effective amount" as used herein refers to a solid form of the compound of formula (I) sufficient to reduce or ameliorate the severity, duration, progression or onset of a disease or condition, delay or arrest the progression of a disease or condition, cause the regression of a disease or condition, or delay the recurrence or progression of a symptom, or enhance or improve the therapeutic effect of another therapy. The precise amount administered to a subject will depend on various factors, such as the given drug or compound, pharmaceutical formulation, route of administration, type of disease, condition, identity of the subject or host being treated, etc., and can still be routinely determined by those skilled in the art. For example, determining an effective amount also depends on the degree, severity and type of cell proliferation. A skilled artisan will be able to determine appropriate dosages based on these and other factors. When co-administered with other therapeutic agents, for example, when co-administered with an anticancer agent, the "effective amount" of any other therapeutic agent will depend on the type of drug used. Appropriate dosages are known for approved therapeutic agents and can be adjusted by a skilled artisan according to the condition of the subject, the type of condition being treated, and the amount of the compound or a pharmaceutically acceptable salt thereof. Where no amount is expressly stated, some amount should be assumed. The effective amount of a solid form of the compound of formula (I) may be 10 μg to 2000 mg. This example is non-limiting.

Solid forms of the compounds of formula (I) may be administered by any suitable method of administration. Suitable methods include oral, intravenous, intramuscular or subcutaneous administration to a subject.

The term "pharmaceutically acceptable excipient" or "pharmaceutically acceptable carrier" as used herein includes any and all solvents, dispersion media, coatings, antibacterial agents, isotonic agents, absorption delaying agents and the like. Using such media and agents for pharmaceutically active substances is well known to those skilled in the art. Unless any conventional media or agents are incompatible with the active ingredients, they are contemplated for being used in the composition herein. Supplementary active ingredients can also be incorporated into the pharmaceutical composition.

Therefore, a solid form of the compound of formula (I) can be administered orally together with a pharmaceutically acceptable carrier such as an inert diluent or an absorbable edible carrier. They can be enclosed in hard or soft shell gelatin capsules, can be compressed into tablets, or can be mixed directly with the patient's food. For oral therapeutic administration, the compound or a pharmaceutically acceptable salt thereof may be combined with one or more excipients, and used as ingestible tablets, buccal tablets, lozenges, capsules, elixirs, suspensions, syrups or wafers, etc. These formulations contain an effective amount of the compound of formula (I) (or a pharmaceutically acceptable salt thereof).

Tablets, lozenges, pills, capsules, etc. may further include: binders such as tragacanth, acacia, cornstarch or gelatin; excipients such as dicalcium phosphate; disintegrants such as cornstarch, potato starch, alginic acid, etc.; lubricants, such as magnesium stearate; or sweeteners, such as sucrose, fructose, lactose or aspartame; or flavoring agents.

A solid form of the compound of formula (I) can also be administered intravenously or intraperitoneally by infusion or injection.

Exemplary pharmaceutical dosage forms for injection or infusion include: sterile aqueous solutions, dispersions, or sterile powders containing an active ingredient which are suitable for the extemporaneous preparation of sterile injection or infusion solutions or dispersions. In any case, the ultimate dosage form should be sterile, fluid and stable under the conditions of manufacture and storage.

Figure 13:
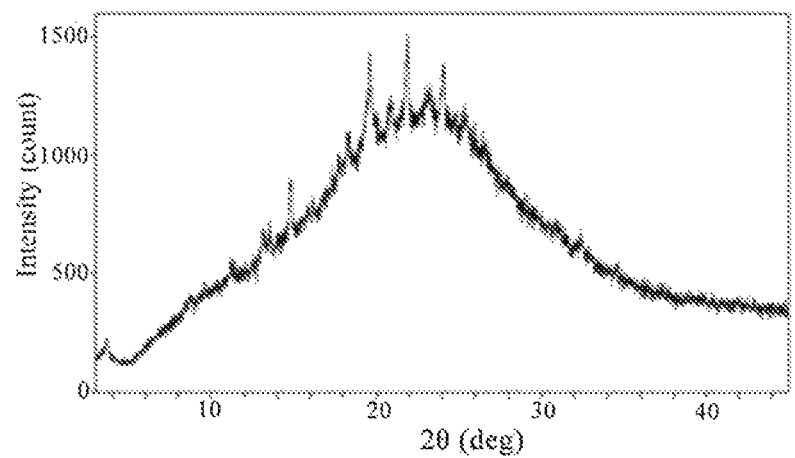
FIG. 13 shows the XRPD pattern of crystalline form II of maleate salt of the compound of formula (I).

The sterile injection solution can be prepared by mixing a required amount of the solid form of the compound (XRPD pattern for the grinding stability of crystalline form I of the tartrate salt in FIG. 13) in an appropriate solvent with the required above-mentioned other ingredients, and then being sterilized by filteration. In the case of sterile powders for the preparation of sterile injection solutions, the preferred methods of preparation may be vacuum drying and freeze-drying technique which can yield a powder of the active ingredient plus any other desired ingredient present after previous sterile filtration.

The amount of solid form of the compound of formula (I) required for treatment may vary not only with the particular salt chosen, but also with the route of administration, the nature of the disease to be treated and the age and condition of the patient, and ultimately can be at the discretion of the attending physician or clinician. In general, however, dosages may range from about 0.1 to about 50 mg/kg body weight per day.

The required dose may conveniently be presented in a single dose or in divided doses administered at appropriate intervals.

As used herein, the term "solid form" and related terms refer to physical forms that are not primarily liquid or gaseous. Solid forms may be crystalline, amorphous or a mixture thereof.

The term "crystalline form" as used herein refers to a crystal form. It includes single component crystalline form and multicomponent crystalline form, and includes, but is not limited to, polymorphs, solvates, and other molecular complexes, as well as salts thereof, solvates of salts, other molecular complexes of salts, and polymorphs of salts. In some embodiments, a crystalline form of a substance may be substantially free of amorphous forms and/or other crystalline forms. In some embodiments, a crystalline form of a substance may contain less than about 1%, 2%, 3%, 4%, 5%, 6%, 7%, 8%, 9%, 10%, 15%, 20%, 25%, 30%, 35%, 40%, 45% or 50% by weight of one or more amorphous forms and/or other crystalline forms. In some embodiments, a crystalline form of a substance may be physically and/or chemically pure. In some embodiments, a crystalline form of a substance may be about 99%, 98%, 97%, 96%, 95%, 94%, 93%, 92%, 91%, or 90% physically and/or chemically pure. In some embodiments, the crystalline form described herein is substantially pure, i.e., substantially free of other crystalline forms and/or other compounds, containing less than about 25%, 20%, 15%, 10%, 9%, 8%, 7%, 6%, 5%, 4%, 3%, 2%, 1%, 0.75%, 0.5%, 0.25% or 0.1% by weight of one or more other crystalline forms and/or other compounds.

Crystalline forms can exhibit different physical characteristic data that are unique to a particular crystalline form, such as the crystalline forms described herein. These characteristic data can be obtained by various techniques known to those skilled in the art, including, for example, X-ray powder diffraction (XRPD), differential scanning calorimetry (DSC), thermogravimetric analysis (TGA) and nuclear magnetic resonance spectroscopy (HNMR). The data provided by these techniques can be used to identify specific crystalline forms. Those skilled in the art can determine whether a crystalline form "matches" the reference data provided herein that are identified as being specific to a particular crystalline form. Characteristic data that "match" the data of the reference crystalline form is understood by those skilled in the art to correspond to the same crystalline form as the reference crystalline form. In the analysis of whether the data "match" or not, those skilled in the art will understand that, due to for example experimental error and routine sample-to-sample analysis, specific characteristic data points may vary to a reasonable extent and still describe a given crystalline form.

"Amorphous" or "amorphous form" and related terms as used herein mean that the substance, component or product is not substantially crystalline as determined by X-ray powder diffraction. In particular, the term "amorphous" describes a disordered solid form, i.e., a solid form that lacks a long-range crystal order. In some embodiments, an amorphous form of a substance may be substantially free of other amorphous forms and/or crystalline forms. In some embodiments, the amorphous form of a substance may contain less than about 1%, 2%, 3%, 4%, 5%, 6%, 7%, 8%, 9%, 10%, 15%, 20%, 25%, 30%, 35%, 40%, 45% or 50% by weight of one or more other amorphous forms and/or crystalline forms. In some embodiments, an amorphous form of a substance may be physically and/or chemically pure. In some embodiments, an amorphous form of a substance may be about 99%, 98%, 97%, 96%, 95%, 94%, 93%, 92%, 91%, or 90% physically and/or chemically pure.

In one aspect, the present disclosure provides a solid form comprising a compound of formula (I) or a salt thereof, or a solvate thereof, or a solvate of a salt thereof, or a mixture thereof:

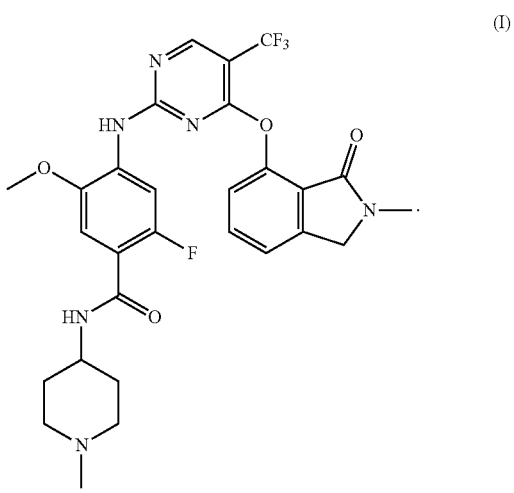

(I)

In some embodiments, a solid form comprising the compound of formula (I) may be a crystalline form, a partially crystalline form, or a mixture of crystalline and amorphous forms. In some embodiments, the solid form may comprise a crystalline form of the compound of formula (I), or a salt thereof, or a solvate thereof, or a solvate of a salt thereof, or a mixture thereof. In some embodiments, the solid form further comprises a co-former. In some embodiments, a co-crystal of the compound of formula (I) and the co-former in a solid form is included. In some embodiments, the solid form is amorphous. In some embodiments, the solid form is substantially pure.

In some embodiments, the solid form comprises a solid form of the free base of the compound of formula (I) or a solvate thereof. In some embodiments, the solid form comprises a solid form of the anhydrous free base of the compound of formula (I). In some embodiments, the solid form comprises a solid form of a solvate of the free base of the compound of formula (I). The compound of formula (I), or a salt thereof, or a solvate thereof, or a solvate of a salt thereof, or a mixture thereof may exist in various solid forms. Such solid forms include crystalline forms, amorphous solids, or mixtures of crystalline and amorphous forms. In some embodiments, the solid form is substantially a crystalline form. In some embodiments, the solid form is a crystalline form.

In some embodiments, the molar ratio of the compound of formula (I) to solvent/water in the solid form ranges from about 10:1 to about 1:10. In some embodiments, the molar ratio of the compound of formula (I) to solvent/water in the solid form ranges from about 5:1 to about 1:5. The molar ratio of the compound of formula (I) to solvent/water in the solid form ranges from about 3:1 to about 1:3. The molar ratio of the compound of formula (I) to solvent/water in the solid form ranges from about 2:1 to about 1:2. In some embodiments, the molar ratio is about 1:2 (i.e., disolvate). In some embodiments, the molar ratio is about 1:1 (i.e., monosolvate). In some embodiments, the molar ratio is about 2:1 (i.e., hemisolvate).

In some embodiments, the solid form is crystalline form A of free base of the compound of formula (I). In some embodiments, crystalline form A of the free base is substantially free of amorphous forms. In some embodiments, crystalline form A of the free base is substantially free of other crystalline forms. In some embodiments, crystalline form A of the free base is substantially free of salts of the compound of formula (I). In some embodiments, crystalline form A of the free base is substantially pure crystalline form A.

In some embodiments, crystalline form A of the free base has X-ray powder diffraction (XRPD) including peaks at 4.8, 9.6, 11.0, 11.5, 17.4, 19.3, 21.6, 22.3, 22.5, and 24.8 degrees 2θ. In some embodiments, crystalline form A of the free base has an XRPD pattern substantially as shown in FIG. 1.

Figure 2A:
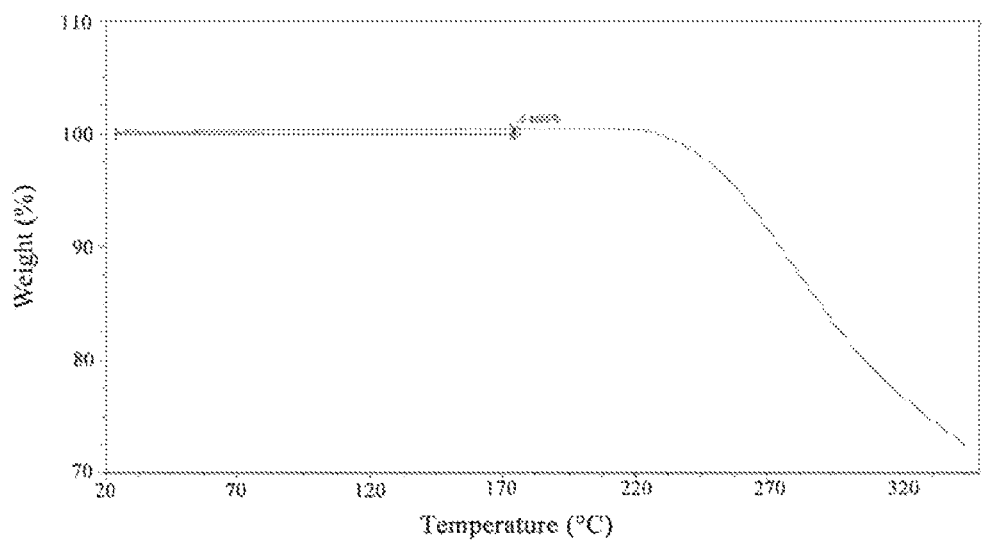
FIG. 2a shows the thermogravimetry analysis (TGA) of crystalline form A of free base of the compound of formula (I)

In some embodiments, crystalline form A of the free base exhibits a weight loss of about 0.46% when heated from about 25° C. to about 172° C. In some embodiments, crystalline form A of the free base has a TGA spectrum substantially as shown in FIG. 2a. From TGA analysis, crystalline form A of free base of the compound of formula (I) is a non-solvate.

Figure 2B:
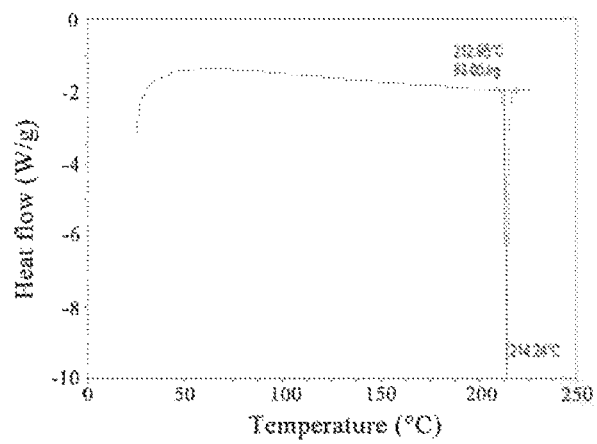
FIG. 2b shows the differential scanning calorimetry (DSC) analysis results of crystalline form A of free base of the compound of formula (I).

In some embodiments, crystalline form A of the free base exhibits an endothermic event as characterized by DSC, with an onset temperature at about 212.95° C. and/or a peak temperature at about 214.24° C. In some embodiments, crystalline form A of the free base has a DSC spectrum substantially as shown in FIG. 2b.

In some embodiments, the solid form is a salt of the compound of formula (I). The compound of formula (I) forms a salt with an acid. The ratio of the compound of formula (I) to an acid may be stoichiometric or non-stoichiometric. In some embodiments, the ratio of the compound of formula (I) to the acid ranges from about 5:1 to about 1:5. In some embodiments, the ratio of the compound of formula (I) to the acid ranges from about 5:1, 4:1, 3:1, 2.5:1, 2:1, 1.5:1, 1:1, 1:1.5, 1:2, 1:2.5, 1:3, 1:4, or 1:5. In some embodiments, the ratio of the compound of formula (I) to the acid is about 1:1. In some embodiments, the acid is one or more of tartaric acid, hydrochloric acid, succinic acid, salicylic acid, sulfuric acid, phosphoric acid, acetic acid, maleic acid, fumaric acid, citric acid, malic acid, lactic acid, gluconic acid, aspartic acid, hippuric acid, glutamic acid, adipic acid, methanesulfonic acid, benzenesulfonic acid, benzoic acid, 2-hydroxyethanesulfonic acid, p-toluenesulfonic acid, 2-naphthalenesulfonic acid and hydrobromic acid. In some embodiments, the acid is one or more of tartaric acid, hydrochloric acid, succinic acid, salicylic acid, and fumaric acid.

Figure 3:
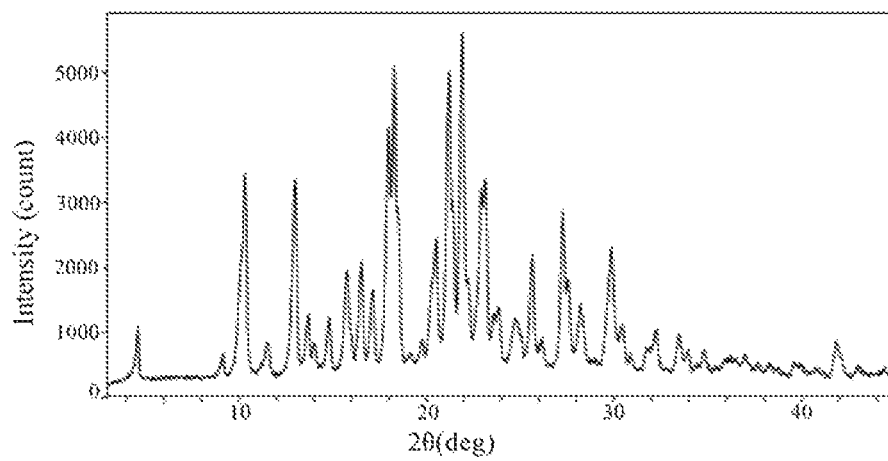
FIG. 3 is the X-ray powder diffraction (XRPD) pattern of crystalline form I of tartrate salt of the compound of formula (I).

In some embodiments, the solid form is the crystalline form of tartrate salt of the compound of formula (I). In some embodiments, the solid form is crystalline form I of tartrate salt of the compound of formula (I). In crystalline form I of tartrate salt of the compound of formula (I), the molar ratio of the compound of formula (I) to tartaric acid is about 1:1. In some embodiments, it has X-ray powder diffraction (XRPD) including peaks at 10.3, 13.0, 18.0, 18.3, 21.2, 21.9, 23.1, 25.7, 27.3, and 30.0 degrees 2θ. In some embodiments, it has an XRPD pattern substantially as shown in FIG. 3.

Figure 4A:
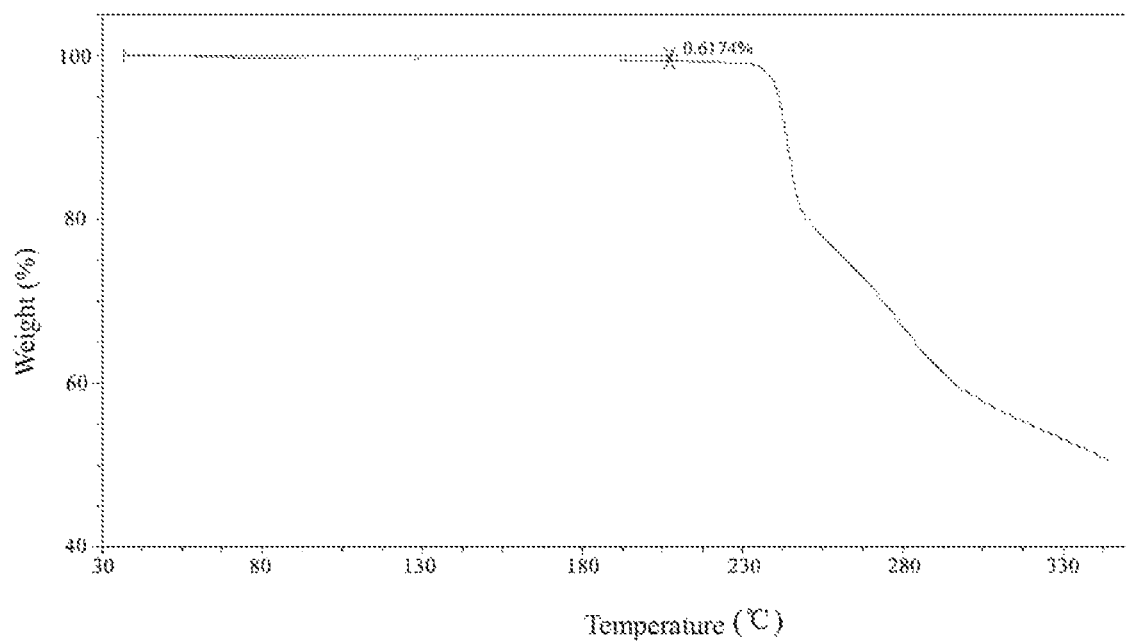
FIG. 4a shows the thermogravimetry analysis (TGA) of crystalline form I of tartrate salt of the compound of formula (I)

In some embodiments, crystalline form I of tartrate salt of the compound of formula (I) exhibits a weight loss of about 0.87% when heated from about 25° C. to about 158° C. In some embodiments, it has a TGA spectrum substantially as shown in FIG. 4a. From TGA analysis, crystalline form I of tartrate salt of the compound of formula (I) is a non-solvate.

Figure 4B:
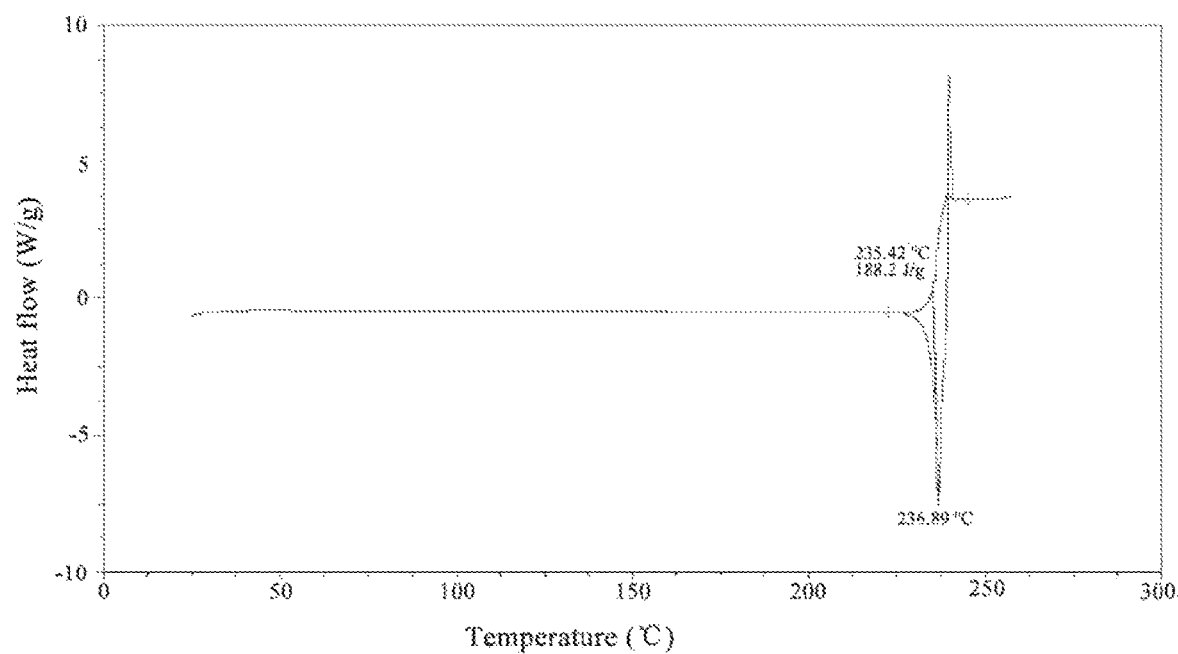
FIG. 4b shows the differential scanning calorimetry (DSC) analysis results of crystalline form I of tartrate salt of the compound of formula (I)

In some embodiments, crystalline form I of tartrate salt of the compound of formula (I) exhibits an endothermic event as characterized by DSC, with an onset temperature at about 235.42° C. and/or a peak temperature at about 235.89° C. In some embodiments, it has a DSC spectrum substantially as shown in FIG. 4b.

Figure 4C:
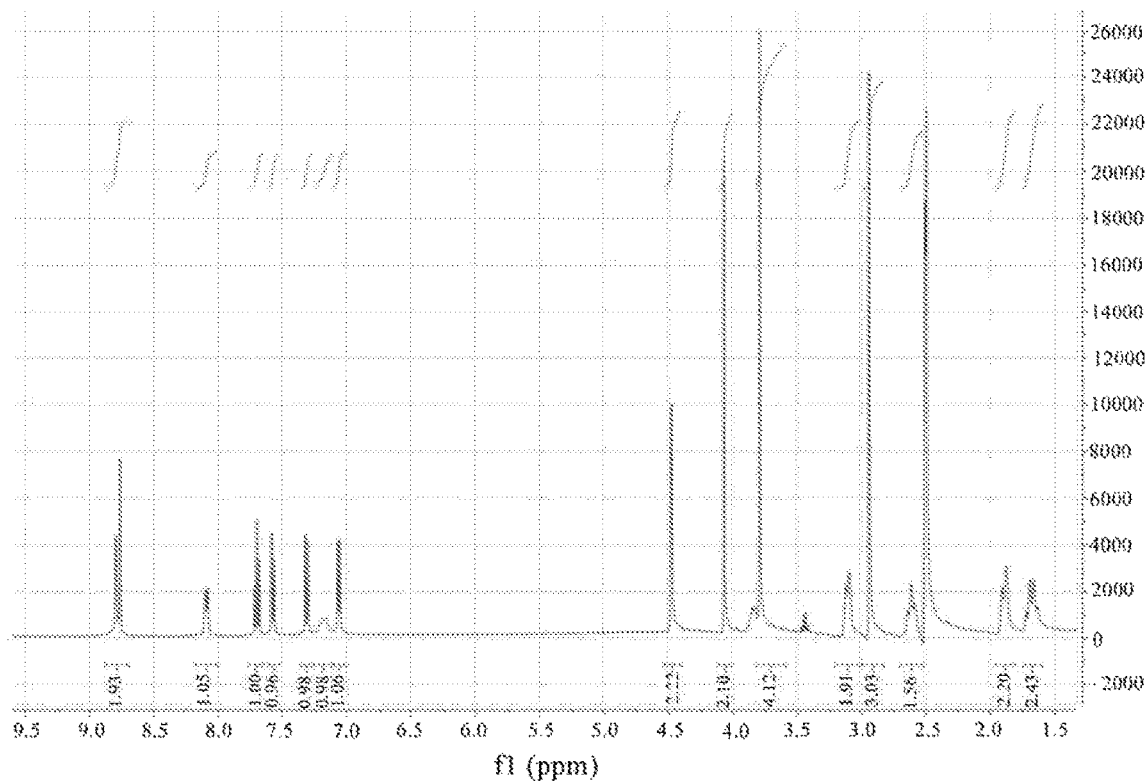
FIG. 4c shows the $^1$H NMR (DMSO-$d_6$) of crystalline form I of tartrate salt of the compound of formula (I)

In some embodiments, crystalline form I of tartrate salt of the compound of formula (I) exhibits a weight gain of about 1% when subjected to an increase in relative humidity from about 0 to about 95% relative humidity. In some embodiments, it has a DVS spectrum substantially as shown in FIG. 4c.

In some embodiments, the present disclosure provides a pharmaceutical combination, characterized in that the pharmaceutical combination comprises the solid form of the compound of formula (I), in particular, an effective amount of the solid form of the compound of formula (I), and a pharmaceutically acceptable excipient.

In some embodiments, the present disclosure provides a use of the solid form of the compound of formula (I) and the pharmaceutical composition described in the present disclosure in the manufacture of a medicament for the treatment of the following diseases: Hodgkin's lymphoma, non-Hodgkin's lymphoma, lung cancer, liver cancer, bile duct cancer, myelodysplastic syndrome, leukemia, thyroid cancer, glioma, colon cancer, rectal cancer, colorectal cancer, ovarian cancer, bladder cancer, prostate cancer, breast cancer, sarcoma, neuroblastoma, renal cell carcinoma, head and neck cancer, gastric cancer, esophageal cancer, gastroesophageal junction cancer, thymus cancer, pancreatic cancer, uterine cancer, testicular cancer, melanoma, skin cancer, mesothelioma, thymoma, germinoma, glioblastoma, nasopharyngeal cancer, oropharyngeal cancer, or laryngeal cancer; especially non-small cell lung cancer, small cell lung cancer, colorectal cancer, pancreatic cancer, leukemia, bladder cancer, cervical cancer, bile duct cancer, esophageal cancer, gastric cancer, glioblastoma, liver cancer, melanoma, mesothelioma, ovarian cancer, prostate cancer, kidney cancer, sarcoma, thyroid cancer, testicular cancer, thymoma, or uterine cancer.

The abbreviations used have the following meanings:

| mg | mg |
| ml | ml |
| TGA | Thermogravimetric Analysis |
| DSC | Differential Scanning Calorimetry |
| DVS | Gravimetric Dynamic Vapor Sorption isotherm plot |

Testing Method

1. X-ray Powder Diffraction (XRPD)

| Instrument model | Rigaku Ultima IV |
| Diffraction line | CuKα (40 kV, 30 mA) |
| Scan rate | 20°/min (2 θ value) |
| Scan range | 3°~45° (2 θ value) |

2. Thermogravimetric Analysis (TGA)

| Instrument model | TA Q500 |
| Heating rate | 10° C./min |

3. Differential Scanning Calorimetry (DSC)

| Instrument model | TA Q2000 |
| Heating rate | 10 C./min |

4. Gravimetric Dynamic Vapor Sorption Isotherm Plot (DVS)

| Instrument model | SMS DVS Intrinsic |
|---|---|
| Temperature | 25° C. |
| Relative Humidity (RH) Variation Control Process | 40-95-0-95-0% |

Example 1: Preparation of Free Base of the Compound of Formula (I)

According to the method disclosed in WO2010058032, free base of the compound of formula (I) was prepared, (M+H)$^+$: 589.

Example 2: Screening of Crystalline Forms of Free Base of the Compound of Formula (I)

For the free base obtained as described above, crystallinity studies and scalability studies were carried out in different solvents. It can be found that the free base has polymorphs. Four polymorphs were obtained within the scope of crystalline form screening, but only crystalline form A can be reproduced when scaled up. Therefore, crystalline form A of the free base is the most preferred crystalline form of the free base of the compound of formula (I).

TABLE 1

Study on the crystallinity of free base of the compound of formula (I)

| | Crystalline form | |
|---|---|---|
| Reagent | Slurry | Evaporation |
| 75% Ethanol | B | B |
| 95% Isopropanol | B | B |
| Water | B | NA |
| 2-Butanone | C | C |
| Methyl tert-butyl ether | A | B |
| Acetone | A | A |
| Ethyl acetate | A | A |
| Isopropanol | A | Amorphous |
| Acetonitrile | A | A |
| Methanol | B | B |
| Tetrahydrofuran | A | A |
| Dioxane | D | B |

The free base (1.7 g) obtained as described above was dissolved in absolute ethanol (170 mL), and stirred at 82-87° C. for 1-2 hours. The solution was cooled to room temperature, and distilled under reduced pressure to remove part of the solvent until a solid was precipitated out. The mixture was then left to stand. The solid was collected and dried to obtain crystalline form A of the free base.

$^1$H NMR (400 MHz, DMSO-d6) δ 8.78 (d, J=12.5 Hz, 2H), 7.98-7.91 (m, 1H), 7.70 (t, J=7.8 Hz, 1H), 7.57 (d, J=7.6 Hz, 1H), 7.31 (d, J=7.9 Hz, 1H), 7.16 (s, 1H), 7.05 (d, J=6.4 Hz, 1H), 4.48 (s, 2H), 3.79 (s, 3H), 3.67 (s, 1H), 2.94 (s, 3H), 2.73 (d, J=11.3 Hz, 2H), 2.16 (s, 3H), 1.94 (t, J=11.2 Hz, 2H), 1.79-1.71 (m, 2H), 1.52 (qd, J=11.9, 3.9 Hz, 2H).

XRPD characterization data of crystalline form A of the free base of the compound of formula (I):

| 2 θ | Spacing | Strength % |
|---|---|---|
| 4.781 | 18.4684 | 27.4 |
| 5.255 | 16.8038 | 13 |
| 6.395 | 13.8099 | 6.4 |
| 7.361 | 11.9993 | 8 |
| 7.619 | 11.5939 | 7.9 |
| 8.818 | 10.02 | 2.1 |
| 9.58 | 9.2247 | 34.6 |
| 10.54 | 8.3863 | 18 |
| 10.979 | 8.0519 | 34.6 |
| 11.459 | 7.7157 | 22.8 |
| 12.34 | 7.167 | 11.1 |
| 12.96 | 6.8254 | 6.9 |
| 13.278 | 6.6626 | 7.7 |
| 14.678 | 6.0299 | 13.1 |
| 15.58 | 5.683 | 5.2 |
| 16.377 | 5.408 | 6.7 |
| 17.402 | 5.0918 | 23.9 |
| 18.54 | 4.7817 | 16.6 |
| 19.26 | 4.6045 | 100 |
| 19.918 | 4.4539 | 16.5 |
| 20.819 | 4.2631 | 10.8 |
| 21.581 | 4.1143 | 54.3 |
| 22.26 | 3.9903 | 33.7 |
| 22.54 | 3.9414 | 25.3 |
| 23.22 | 3.8275 | 5.9 |
| 23.521 | 3.7792 | 14.9 |
| 24.217 | 3.6721 | 18.6 |
| 24.801 | 3.587 | 53.6 |
| 25.181 | 3.5337 | 12.5 |
| 26.101 | 3.4112 | 4.8 |
| 26.439 | 3.3683 | 4.3 |
| 27.38 | 3.2547 | 10.5 |
| 28.543 | 3.1247 | 5 |
| 29.219 | 3.0538 | 17.8 |
| 29.721 | 3.0035 | 5.8 |
| 31.4 | 2.8466 | 4.1 |
| 31.717 | 2.8188 | 2.5 |
| 32.621 | 2.7428 | 6.1 |
| 33.118 | 2.7027 | 3.5 |
| 33.458 | 2.676 | 2.2 |
| 34.462 | 2.6003 | 2.8 |
| 35.178 | 2.549 | 1.9 |
| 35.658 | 2.5158 | 3.9 |
| 36.556 | 2.456 | 1.5 |
| 36.999 | 2.4276 | 3.5 |
| 39.335 | 2.2887 | 1.3 |
| 39.836 | 2.261 | 2.4 |
| 43.02 | 2.1008 | 2.6 |
| 44.279 | 2.0439 | 1.9 |

Example 3: Screening of Crystalline Forms of Salts of the Compound of Formula (I)

3.1 Preparation of Acid Solution

According to the solubility of different acids, acid solutions were prepared respectively, as follows:

sulfuric acid, phosphoric acid, acetic acid, maleic acid, tartaric acid, citric acid, malic acid, lactic acid, gluconic acid, adipic acid, methanesulfonic acid, benzenesulfonic acid, benzoic acid, 2-hydroxyethanesulfonic acid, p-toluenesulfonic acid, hydrobromic acid: a solution in methanol with a concentration of 1 mol/L;

aspartic acid, hippuric acid, glutamic acid: a solution in water with a concentration of 0.02 mol/L;

2-naphthalenesulfonic acid: a solution in water with a concentration of 0.01 mol/L.

Crystalline form A of the free base (17.6 mg, about 0.03 mmol) was added to a 10 mL sample bottle, and an appropriate amount of reaction solvent was added. The mixture was dissolved by stirring, and then acid solutions (at a reaction molar ratio of 1:1) were added, respectively. The mixture was reacted at 50° C. for 3 h. The reaction solution was then cooled to room temperature, further stirred overnight, and then placed in a refrigerator at 4° C. to stand for 8 h. The samples without solid precipitation were volatilized at room temperature to obtain a solid, which was then measured by XRPD. The samples with solid precipitation were centrifuged to remove the solvent. The solid obtained by centrifugation and the solid obtained by volatilization of the supernatant were dried separately and then subjected to XRPD measurement to determine whether a salt was formed. The results are shown in Table 2.

Figure 8:
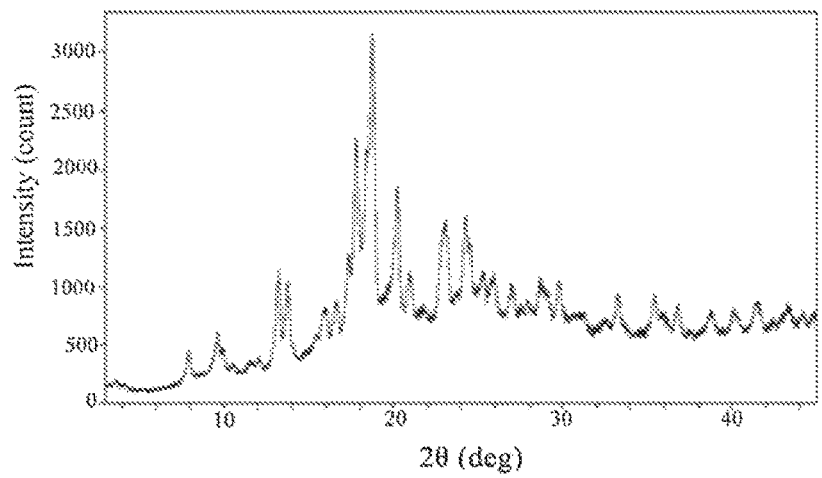
FIG. 8 shows the XRPD pattern of crystalline form D of free base of the compound of formula (I).
Figure 9:
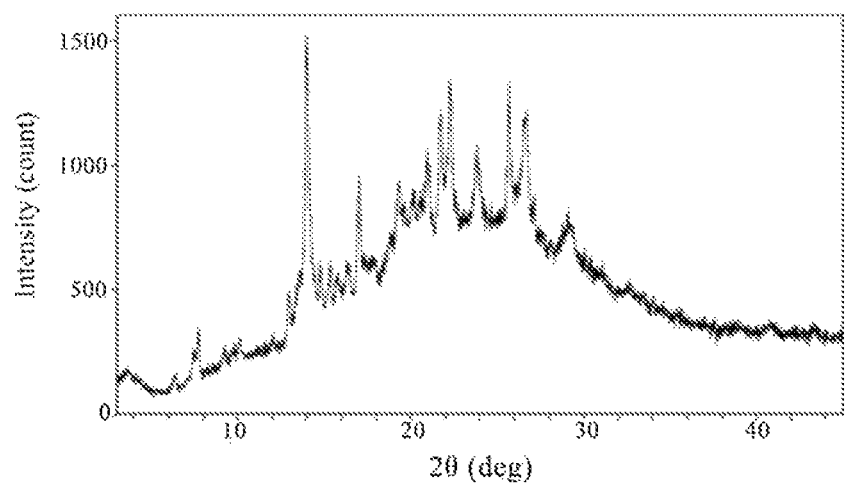
FIG. 9 shows the XRPD pattern of crystalline form I of sulfate salt of the compound of formula (I).
Figure 10:
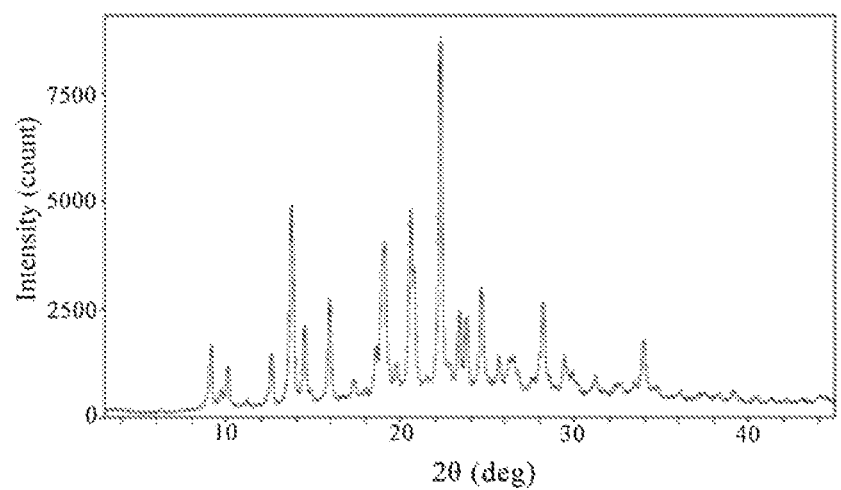
FIG. 10 shows the XRPD pattern of crystalline form I of phosphate salt of the compound of formula (I).
Figure 11:
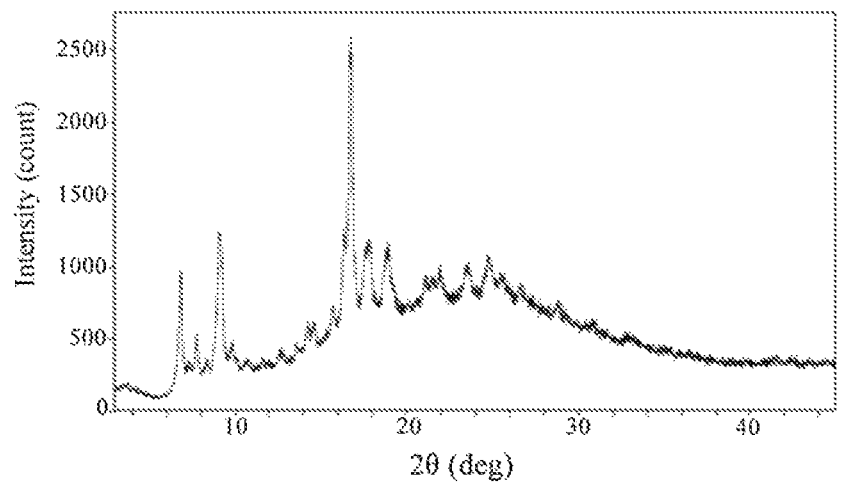
FIG. 11 shows the XRPD pattern of crystalline form II of phosphate salt of the compound of formula (I).
Figure 12:
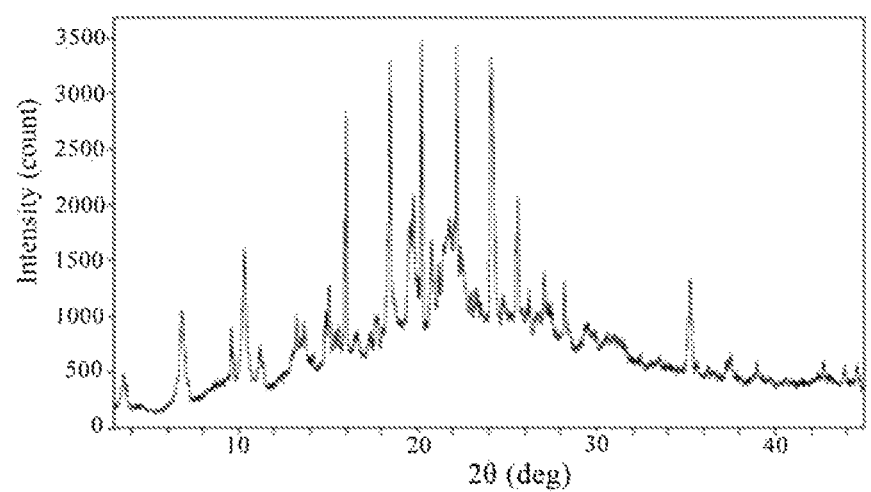
FIG. 12 shows the XRPD pattern of crystalline form I of maleate salt of the compound of formula (I).

FIG. 8 shows the XRPD pattern of crystalline form D of free base of the compound of formula (I).
FIG. 9 shows the XRPD pattern of crystalline form I of sulfate salt of the compound of formula (I).
FIG. 10 shows the XRPD pattern of crystalline form I of phosphate salt of the compound of formula (I).
FIG. 11 shows the XRPD pattern of crystalline form II of phosphate salt of the compound of formula (I).
FIG. 12 shows the XRPD pattern of crystalline form I of maleate salt of the compound of formula (I).

TABLE 2

Screening results of acid addition salts of the compound of formula (I)

| | Acid | | | | | | | |
|---|---|---|---|---|---|---|---|---|
| | Sulfuric acid | | Phosphoric acid | | Acetic acid | | Maleic acid | |
| Solvent | Precipitation | Volatilization | Precipitation | Volatilization | Precipitation | Volatilization | Precipitation | Volatilization |
| 75% Ethanol | NA | Amorphous | NA | Amorphous | NA | B | NA | Amorphous |
| Acetone | NA | Amorphous | I | NA | NA | B | NA | II |
| Ethyl acetate | I | Amorphous | II | C | NA | C | NA | I |

| | Acid | | | | | | | |
|---|---|---|---|---|---|---|---|---|
| | Tartaric acid | | Citric acid | | Lactic acid | | Malic acid | |
| Solvent | Precipitation | Volatilization | Precipitation | Volatilization | Precipitation | Volatilization | Precipitation | Volatilization |
| 75% Ethanol | NA | I | NA | Amorphous | NA | I | NA | Amorphous |
| Acetone | I | NA | NA | Amorphous | NA | Amorphous | NA | Amorphous |
| Ethyl acetate | I | I | I | I | NA | I | NA | Amorphous |

| | Acid | | | | | | | |
|---|---|---|---|---|---|---|---|---|
| | Gluconic acid | | Hippuric acid | | Glutamic acid | | Aspartic acid | |
| Solvent | Precipitation | Volatilization | Precipitation | Volatilization | Precipitation | Volatilization | Precipitation | Volatilization |
| 75% Ethanol | NA | Amorphous | NA | Amorphous | NA | Amorphous | NA | Amorphous |
| Acetone | NA | B | NA | Amorphous | NA | Amorphous | NA | Amorphous |
| Ethyl acetate | NA | C | NA | Amorphous | NA | Amorphous | NA | Amorphous |

| | Acid | | | | | | | |
|---|---|---|---|---|---|---|---|---|
| | Adipic acid | | Methanesulfonic acid | | Benzenesulfonic acid | | 2-hydroxyethanesulfonic | |
| Solvent | Precipitation | Volatilization | Precipitation | Volatilization | Precipitation | Volatilization | Precipitation | Volatilization |
| 75% Ethanol | NA | Amorphous | NA | Amorphous | NA | Amorphous | NA | Amorphous |
| Acetone | NA | Amorphous | NA | Amorphous | NA | I | NA | Amorphous |
| Ethyl acetate | NA | Amorphous | NA | Amorphous | Amorphous | I | I | Amorphous |

| | Acid | | | | | | | |
|---|---|---|---|---|---|---|---|---|
| | Benzoic acid | | p-Toluenesulfonic acid | | 2-Naphthalenesulfonic acid | | Hydrobromic acid | |
| Solvent | Precipitation | Volatilization | Precipitation | Volatilization | Precipitation | Volatilization | Precipitation | Volatilization |
| 75% Ethanol | NA | I | NA | B | B | NA | NA | Amorphous |
| Acetone | NA | I | NA | I | B | NA | NA | Amorphous |
| Ethyl acetate | NA | I | NA | B | NA | Amorphous | I | Amorphous |

Note: The I or II mentioned in the above table are different crystalline forms of the respective acids after the corresponding acid radicals are salified. For example, when the acid is sulfuric acid and the solvent is ethyl acetate, crystalline form I obtained by precipitation is crystalline form I of the sulfate salt, and so on for other crystalline forms. The A, B and C are all crystalline forms of the free base of the compound. NA means no sample was acquired.

Figure 6:
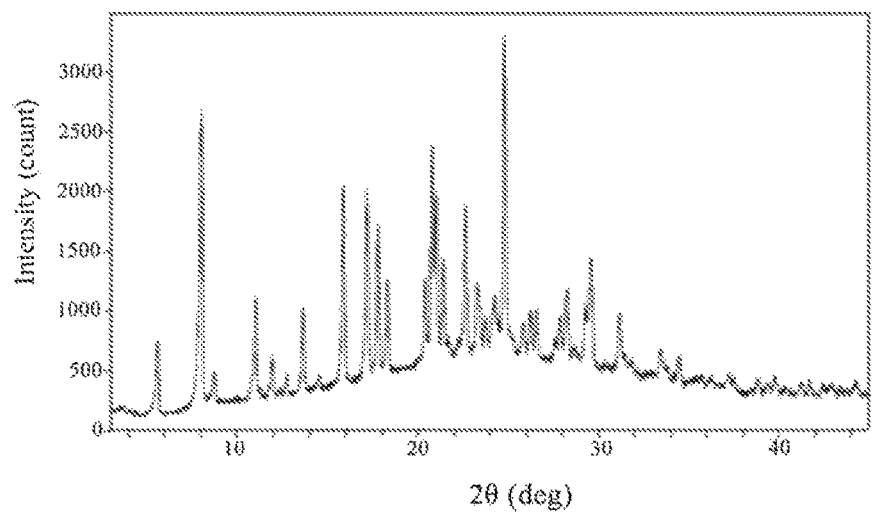
FIG. 6 shows the XRPD pattern of crystalline form B of free base of the compound of formula (I).
Figure 7:
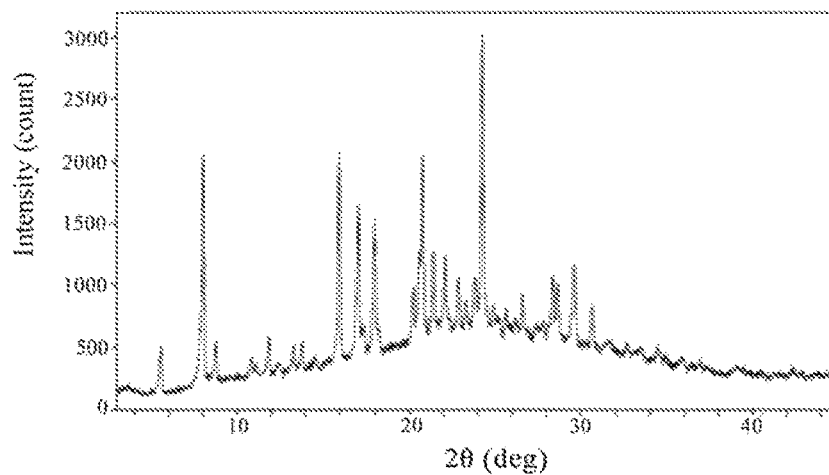
FIG. 7 shows the XRPD pattern of crystalline form C of free base of the compound of formula (I).
Figure 14:
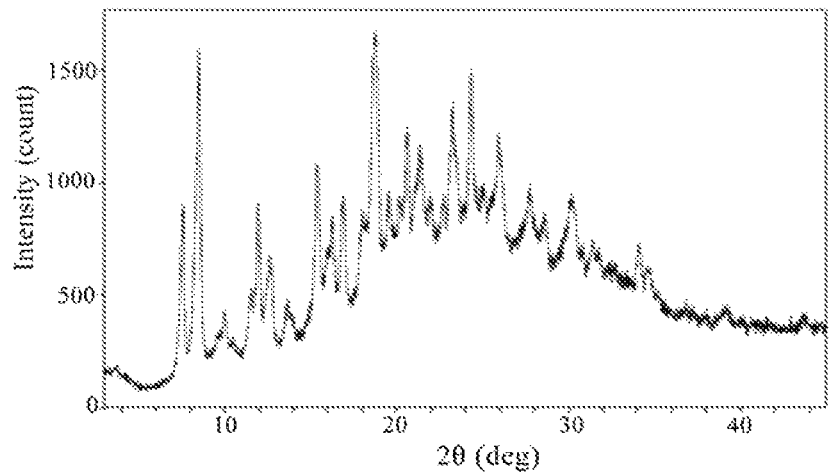
FIG. 14 shows the XRPD pattern of crystalline form I of citrate salt of the compound of formula (I).
Figure 15:
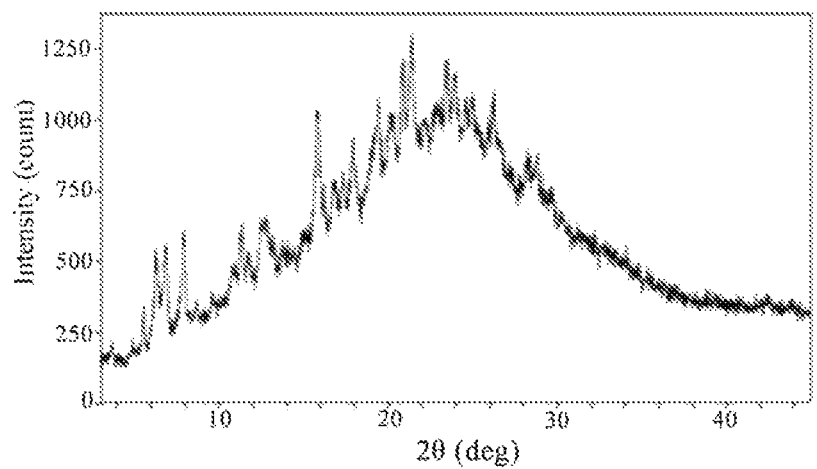
FIG. 15 shows the XRPD pattern of crystalline form I of lactate salt of the compound of formula (I).
Figure 16:
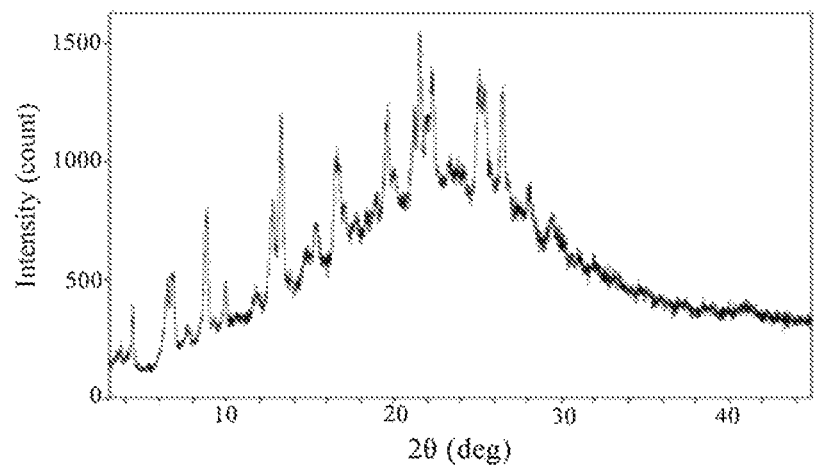
FIG. 16 shows the XRPD pattern of crystalline form I of benzenesulfonate salt of the compound of formula (I).
Figure 17:
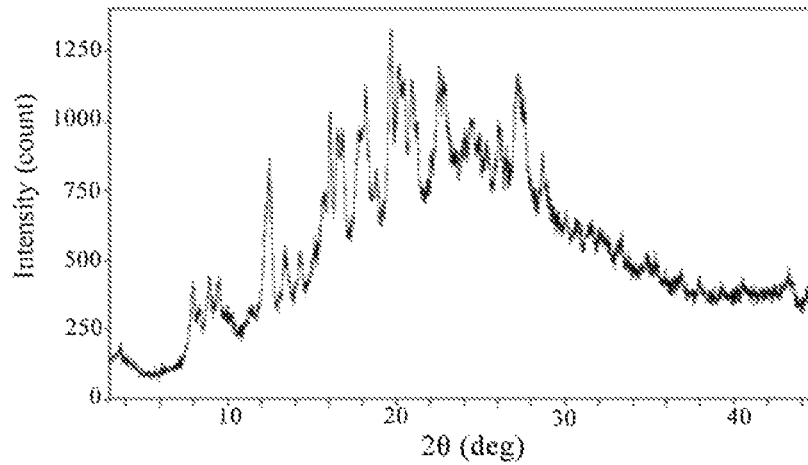
FIG. 17 shows the XRPD pattern of crystalline form I of 2-hydroxyethanesulfonate salt of the compound of formula (I).

FIG. 6 shows the XRPD pattern of crystalline form B of free base of the compound of formula (I).
FIG. 7 shows the XRPD pattern of crystalline form C of free base of the compound of formula (I).
FIG. 13 shows the XRPD pattern of crystalline form II of maleate salt of the compound of formula (I).
FIG. 14 shows the XRPD pattern of crystalline form I of citrate salt of the compound of formula (I).
FIG. 15 shows the XRPD pattern of crystalline form I of lactate salt of the compound of formula (I).
FIG. 16 shows the XRPD pattern of crystalline form I of benzenesulfonate salt of the compound of formula (I).
FIG. 17 shows the XRPD pattern of crystalline form I of 2-hydroxyethanesulfonate salt of the compound of formula (I).

Figure 18:
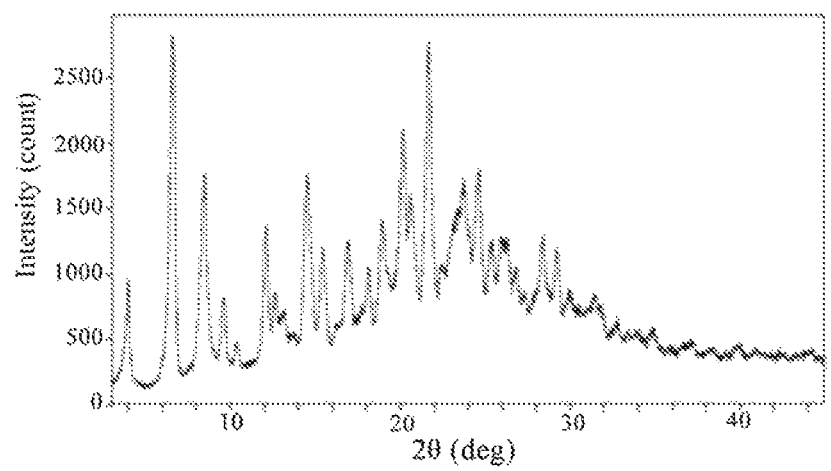
FIG. 18 shows the XRPD pattern of crystalline form I of benzoate salt of the compound of formula (I).

FIG. 18 shows the XRPD pattern of crystalline form I of benzoate salt of the compound of formula (I).

Figure 19:
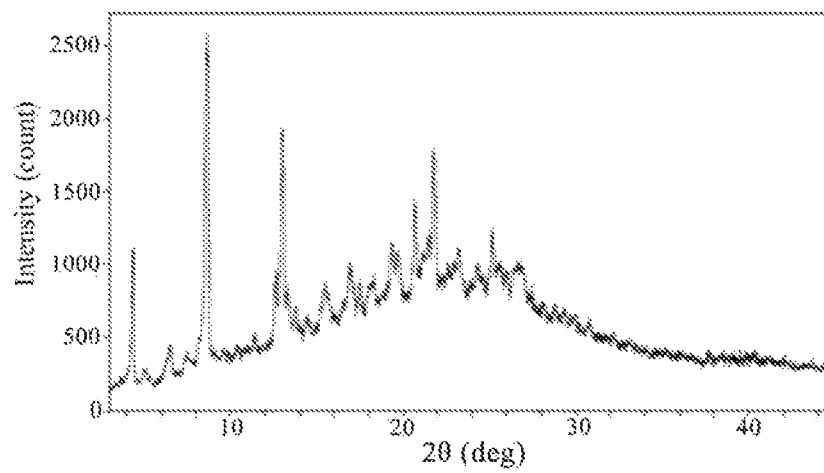
FIG. 19 shows the XRPD pattern of crystalline form I of p-toluenesulfonate salt of the compound of formula (I).

FIG. 19 shows the XRPD pattern of crystalline form I of p-toluenesulfonate salt of the compound of formula (I).

Figure 20:
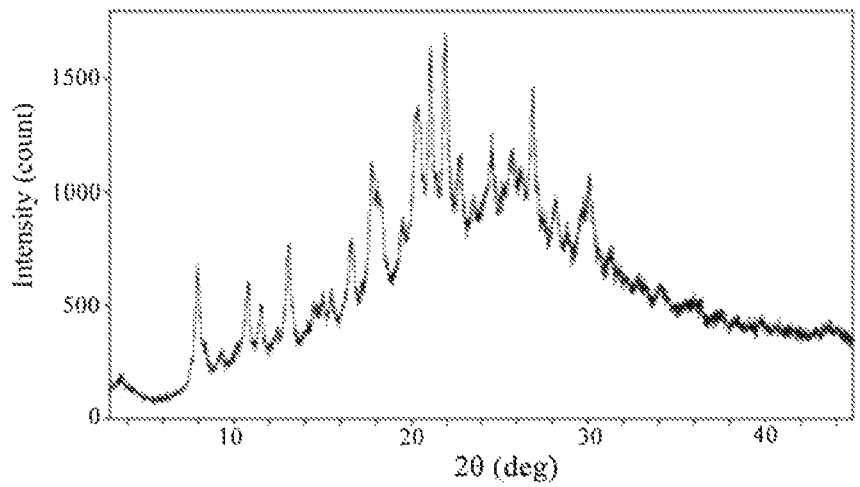
FIG. 20 shows the XRPD pattern of crystalline form I of hydrobromide salt of the compound of formula (I).

FIG. 20 shows the XRPD pattern of crystalline form I of hydrobromide salt of the compound of formula (I).

Example 4: Preparation of Crystalline Form I of Tartrate Salt of the Compound of Formula (I)

In addition to preparing crystalline form I by the method in the screening results of acid addition salts as described above, it can also be prepared as follows.

The free base (2.5 g) obtained as described above and tartaric acid (0.65 g) were dissolved in 75% ethanol (180 mL). The mixture was stirred at 55-65° C. for 1-3 hours, and then cooled to room temperature. The solution was distilled under reduced pressure to remove part of the solvent until a solid was precipitated, and then left to stand. The solid was collected and dried to afford crystalline form I of the tartrate salt. In crystalline form I of tartrate salt of the compound of formula (I), the molar ratio of the compound of formula (I) to tartaric acid was about 1:1.

$^1$H NMR (400 MHZ, DMSO-d6) δ 8.78 (d, J=15.1 Hz, 2H), 8.06 (d, J=7.4 Hz, 1H), 7.70 (t, J=7.8 Hz, 1H), 7.57 (d, J=7.6 Hz, 1H), 7.31 (d, J=7.9 Hz, 1H), 7.18 (d, J=13.8 Hz, 1H), 7.06 (d, J=6.5 Hz, 1H), 4.48 (s, 2H), 4.03 (s, 2H), 3.79 (s, 4H), 3.01 (d, J=11.5 Hz, 2H), 2.94 (s, 3H), 2.41 (s, 3H), 1.86 (d, J=12.3 Hz, 2H), 1.62 (q, J=11.8 Hz, 2H).

XRPD characterization data of crystalline form I of the tartrate salt:

| 2 θ | Spacing | Strength % |
| --- | --- | --- |
| 4.637 | 19.0415 | 17.9 |
| 9.143 | 9.6641 | 7.3 |
| 10.34 | 8.5481 | 66.3 |
| 11.56 | 7.6488 | 10.4 |
| 13.019 | 6.7945 | 61.7 |
| 13.7 | 6.4582 | 16.8 |
| 14.039 | 6.3028 | 7.6 |
| 14.838 | 5.9653 | 17 |
| 15.76 | 5.6184 | 30.5 |
| 16.54 | 5.3551 | 32.9 |
| 17.159 | 5.1633 | 23.2 |
| 17.981 | 4.9291 | 77.5 |
| 18.281 | 4.8488 | 97.4 |
| 19.14 | 4.6333 | 2.7 |
| 19.795 | 4.4812 | 5.6 |
| 20.538 | 4.321 | 34.8 |
| 21.2 | 4.1874 | 82.3 |
| 21.901 | 4.055 | 100 |
| 23.121 | 3.8437 | 55.9 |
| 23.879 | 3.7233 | 15 |
| 24.721 | 3.5984 | 13.8 |
| 25.659 | 3.4689 | 35 |
| 26.179 | 3.4012 | 7.6 |
| 27.299 | 3.2642 | 48.9 |
| 27.541 | 3.236 | 27.1 |
| 28.22 | 3.1597 | 17 |
| 29.879 | 2.9879 | 38.5 |
| 30.459 | 2.9323 | 11.6 |
| 31.723 | 2.8183 | 7.2 |
| 32.277 | 2.7712 | 13.9 |
| 33.479 | 2.6744 | 12.3 |
| 33.941 | 2.639 | 6.8 |
| 34.802 | 2.5757 | 6.7 |
| 35.401 | 2.5335 | 1.4 |
| 36.234 | 2.4771 | 3.9 |
| 36.536 | 2.4573 | 3.7 |
| 37 | 2.4276 | 4.4 |
| 37.666 | 2.3862 | 2.7 |
| 38.296 | 2.3484 | 3.5 |
| 38.777 | 2.3203 | 2.4 |
| 39.602 | 2.2739 | 4.7 |
| 39.94 | 2.2554 | 3.6 |
| 40.877 | 2.2059 | 2.6 |
| 41.821 | 2.1582 | 11.8 |
| 42.981 | 2.1026 | 3.5 |
| 44.403 | 2.0385 | 3.1 |

Example 5: Preparation of Crystalline Form III of Tartrate Salt of the Compound of Formula (I)

In addition to preparing crystalline form III by the method in the screening results of acid addition salts as described above, it can also be prepared as follows:

The free base (2.95 g) obtained as described above was dissolved in ethyl acetate (188 mL), and heated to 60-65° C. A 5 ml solution of tartaric acid in methanol was added dropwise, and the mixture was stirred for 1-3 hours. The reaction solution was cooled to room temperature, filtered, and dried to afford crystalline form III of the tartrate salt. In crystalline form III of tartrate salt of the compound of formula (I), the molar ratio of the compound of formula (I) to tartaric acid was about 1:1.

$^1$H NMR (400 MHz, DMSO-d6) δ 8.78 (d, J=12.9 Hz, 2H), 8.03 (d, J=7.6 Hz, 1H), 7.70 (t, J=7.8 Hz, 1H), 7.57 (d, J=7.6 Hz, 1H), 7.31 (d, J=8.0 Hz, 1H), 7.18 (s, 1H), 7.06 (d, J=6.5 Hz, 1H), 4.48 (s, 2H), 3.97 (s, 2H), 2.95 (d, J=12.4 Hz, 5H), 2.36 (s, 5H), 1.84 (d, J=12.7 Hz, 2H), 1.61 (d, J=11.3 Hz, 2H).

XRPD characterization data of crystalline form III of the tartrate salt:

| 2 θ | Spacing | Strength % |
| --- | --- | --- |
| 6.159 | 14.3388 | 2.2 |
| 7.339 | 12.0355 | 15.5 |
| 8.939 | 9.8841 | 25.5 |
| 10.179 | 8.6833 | 11.7 |
| 11.199 | 7.894 | 20.1 |
| 11.481 | 7.7011 | 5 |
| 13.2 | 6.7016 | 50.2 |
| 13.519 | 6.5444 | 29.1 |
| 14.02 | 6.3115 | 21.2 |
| 14.719 | 6.0132 | 9 |
| 15.181 | 5.8315 | 41.7 |
| 16.461 | 5.3809 | 10 |
| 17.64 | 5.0237 | 15.3 |
| 17.999 | 4.9242 | 16.9 |
| 18.539 | 4.7819 | 34.2 |
| 19.22 | 4.614 | 11.3 |
| 19.479 | 4.5533 | 11.2 |
| 20.019 | 4.4317 | 100 |
| 20.442 | 4.3409 | 6.7 |
| 20.921 | 4.2426 | 26.4 |
| 21.619 | 4.1071 | 16.5 |
| 22.521 | 3.9448 | 55.5 |
| 23.219 | 3.8276 | 39.4 |
| 23.518 | 3.7796 | 6.3 |
| 24.019 | 3.7019 | 4.8 |
| 24.9 | 3.5729 | 69.3 |
| 25.281 | 3.5199 | 4.4 |
| 25.9 | 3.4372 | 6.7 |
| 26.419 | 3.3708 | 13.1 |
| 26.62 | 3.3459 | 13.2 |
| 28.198 | 3.162 | 2.8 |
| 28.978 | 3.0787 | 8.1 |
| 29.703 | 3.0052 | 2.5 |
| 30.779 | 2.9025 | 9.1 |

-continued

| 2 θ | Spacing | Strength % |
|---|---|---|
| 31.202 | 2.8642 | 7.2 |
| 32.357 | 2.7645 | 3.4 |
| 33.117 | 2.7028 | 1.9 |
| 33.819 | 2.6483 | 2 |
| 34.183 | 2.6209 | 2.3 |
| 35.116 | 2.5534 | 2 |
| 36.059 | 2.4887 | 1.4 |
| 36.519 | 2.4584 | 3.5 |
| 37.219 | 2.4138 | 3.1 |
| 38.061 | 2.3623 | 3.7 |
| 39.161 | 2.2984 | 1.3 |
| 40.659 | 2.2172 | 1.5 |
| 41.654 | 2.1665 | 1.4 |
| 41.903 | 2.1542 | 1.5 |
| 43.139 | 2.0953 | 1.5 |

Example 6: Solubility Test

A certain amount of crystalline form A of free base of the compound of formula (I), crystalline form I of the tartrate salt, and crystalline form III of the tartrate salt were weighed and placed in a 5 mL sample bottle. Deionized water, pH 2.0 glycine-hydrochloric acid buffer solution, pH 4.5 $Na_2HPO_4$-citric acid buffer solution, and pH 6.8 $Na_2HPO_4$-citric acid buffer solution were added respectively (each 2 mL). The mixture was placed on a shaker at 25° C., shaken for 24 hours, and then filtered. The filtrate was tested for solubility by HPLC; and the solid was detected by XRPD to determine whether the crystalline form was transformed.

The chromatographic conditions were as follows:
Chromatographic column: Unitary C18 (5 μm, 100A, 4.6×250 mm)
Mobile phase: Phase A was ammonium acetate with pH of 6.2, and phase B was acetonitrile, A:B=10:90.
Detection wavelength: 230 nm, Column temperature: 35° C.
Injection volume: 20 μL
The results of solubility test were shown in Table 3:

TABLE 3

Solubility of free base and salt of the compound of formula (I) (25° C., mg/mL)

| Medium | Crystalline form A of the free base | Crystalline form I of the tartrate salt | Crystalline form III of the tartrate salt |
|---|---|---|---|
| pH 2.0 | >10 | >10 | >10 |
| pH 4.5 | >10 | 5.2 | >10 |
| pH 6.8 | 1.06 | >10 | >10 |
| Deionized water | 0.033 | 2.59 | >10 |

The results of the solubility test show that compared with the free base, the solubility of crystalline form I of the tartrate salt is significantly improved in both deionized water and pH 6.8 buffered saline solution. The solubility of the above crystalline forms is significantly improved in both deionized water and pH 6.8 buffered saline solution. The increased solubility in deionized water greatly reduces formulation difficulty; and the increased solubility in pH 6.8 buffered saline solution greatly increases the oral bioavailability of the drug. As detected by XRPD, no crystal transformation occurs for crystalline form A of the free base in pH 6.8 buffered saline solution and deionized water; and no crystal transformation occurs for crystalline form I of the tartrate salt in deionized water.

Example 7: Evaluation of Accelerated Stability Test

According to the stability test requirements for the raw drug in the fourth part of the 2015 edition of the "Chinese Pharmacopoeia", "Guiding Principles for the Stability Test of Raw Drugs and Preparations", the influence factor test and the accelerated test were investigated on crystalline form.

High temperature test (T): The powder was placed in a suitable sealed glass bottle, and placed at 60° C. for 10 days. Samples were taken on the 5th and 10th day to detect the solid XRPD.

High humidity test (H): The powder was placed in an open constant temperature and humidity box, and placed at 25° C., 90%±5% RH for 10 days. Samples were taken on the 5th and 10th day and the solid XRPD was detected so as to investigate the moisture absorption and deliquescence performances.

Strong light irradiation test (L): The powder was placed in an open box equipped with a fluorescent lamp, and placed under the condition of an illumination of 4500±500 lx for 10 days. Samples were taken on the 5th and 10th day to detect the solid XRPD.

Accelerated test (A): The powder was placed in an open constant temperature and humidity box, and placed at 40° C., 75%±5% RH for 10 days. Samples were taken on the 5th and 10th day to detect the solid XRPD.

Figure 21:
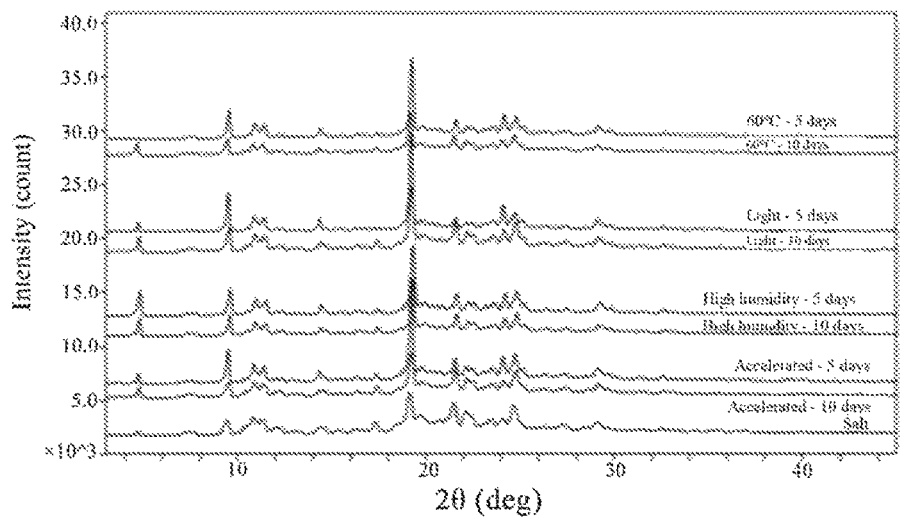
FIG. 21 is the stability analysis of crystalline form A of the free base.
Figure 22:
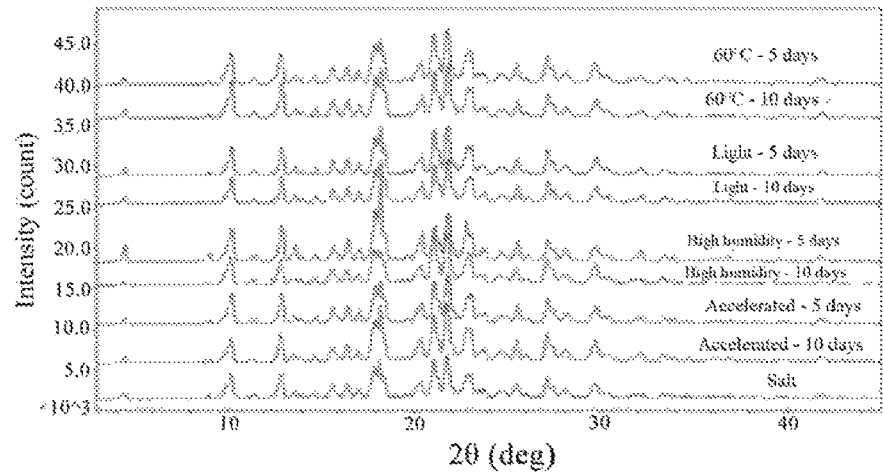
FIG. 22 is the stability analysis of crystalline form I of the tartrate salt.
Figure 23:
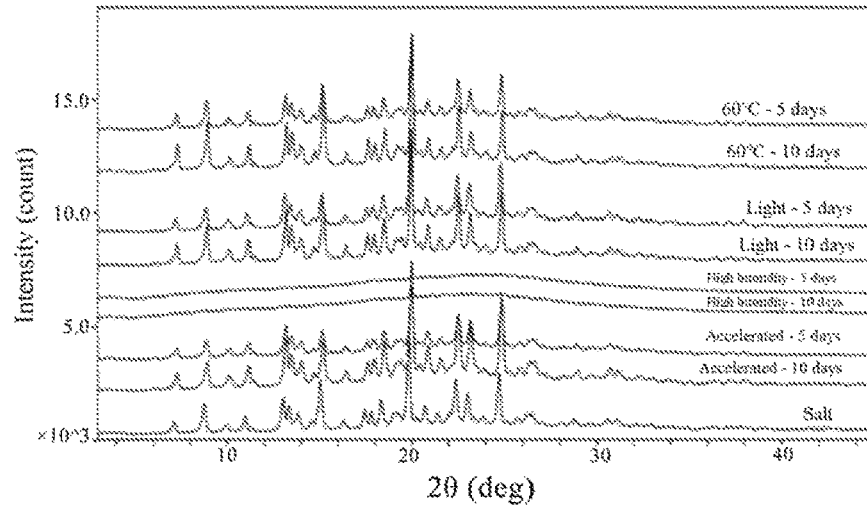
FIG. 23 is the stability analysis of crystalline form III of the tartrate salt.

The results of the stability test were shown in Table 4, and the diagrams were shown in FIGS. 21-23 for details.

TABLE 4

Results of the stability test of crystalline forms

| Condition | Time | Crystalline form A of the free base | Crystalline form I of the tartrate salt | Crystalline form III of the tartrate salt |
|---|---|---|---|---|
| High temperature (60° C.) | 5 days | Consistent | Consistent | Consistent |
| | 10 days | Consistent | Consistent | Consistent |
| High humidity (92.5% RH) | 5 days | Consistent | Consistent | Consistent |
| | 10 days | Consistent | Consistent | Consistent, crystallinity was significantly reduced |
| Strong light (4500 lx) | 5 days | Consistent | Consistent | Consistent |
| | 10 days | Consistent | Consistent | Consistent |
| Accelerated (40° C./75%) | 5 days | Consistent | Consistent | Consistent |
| | 10 days | Consistent | Consistent | Consistent |

The stability results show that crystalline form A of the free base, crystalline form I of the tartrate salt, and crystalline form III of the tartrate salt are all stable under above test conditions without crystal transformation. However, crystallinity of crystalline form III of the tartrate salt is reduced in the high-humidity environment, indicating that for the storage of crystalline form III, attention should be paid to an ambient humidity, otherwise crystalline form III may transform into an amorphous form.

Figure 24:
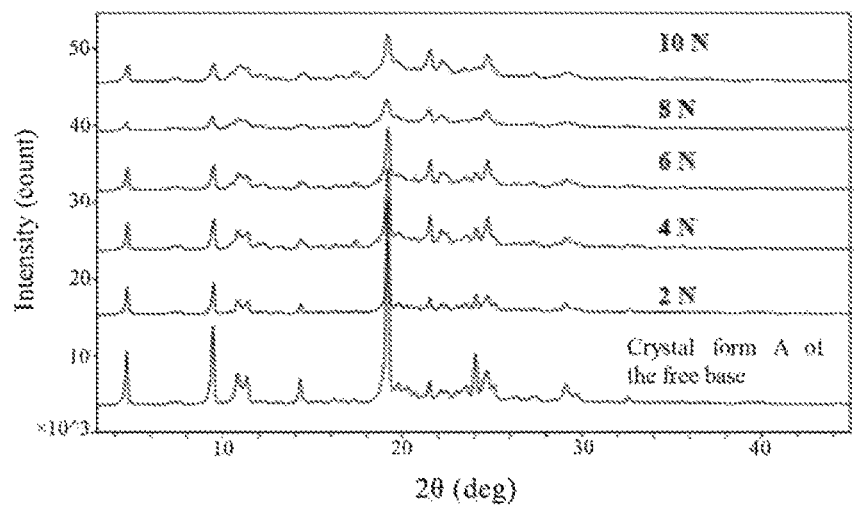
FIG. 24 is the XRPD pattern for the stress stability of crystalline form A of the free base.
Figure 25:
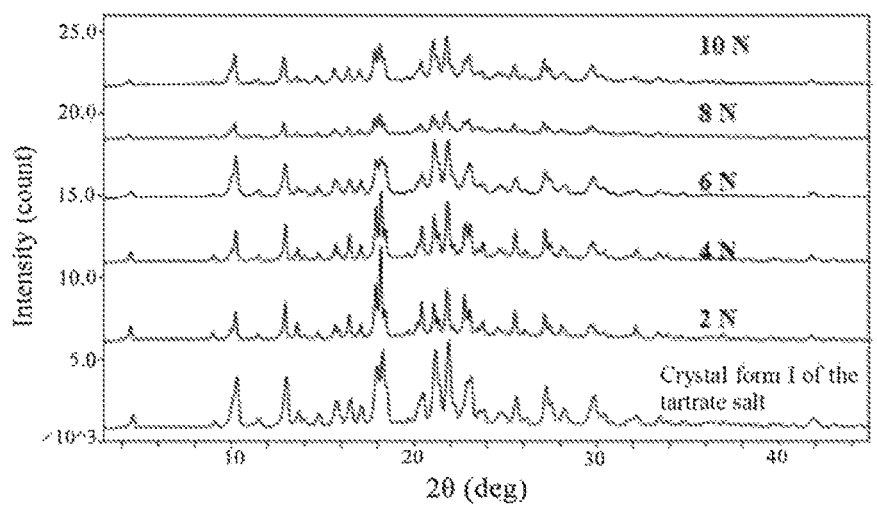
FIG. 25 is the XRPD pattern for the stress stability of crystalline form I of the tartrate salt.
Figure 26:
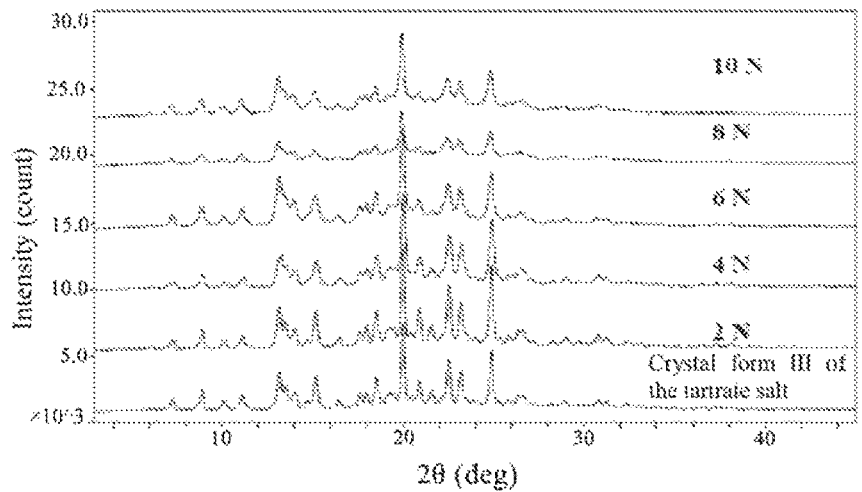
FIG. 26 is the XRPD pattern for the stress stability of crystalline form III of the tartrate salt.

Example 8: Stability Study Under Mechanical Stress 8.1 Stability Under Pressure Condition An appropriate amount of powders of crystalline form A of the free base, crystalline form I of the tartrate salt, and crystalline form III of the tartrate salt were weighed and evenly spread on the bottom of the mold of a powder tablet press. To simulate the pressure conditions in a formulation process, mechanical pressures of 2, 4, 6, 8, and 10 N were applied respectively. The pressure was kept stable for 5 minutes, and then samples were taken for XRPD to investigate the stability of the crystalline form under pressure conditions. For details of patterns, see FIGS. 24-26. Comparison of XRPD results shows that the crystalline forms of crystalline form A of the free base, crystalline form I of the tartrate salt, and the tartrate form III of the tartrate salt are all stable under pressure conditions.

8.2 Stability Under Grinding Condition

Figure 27:
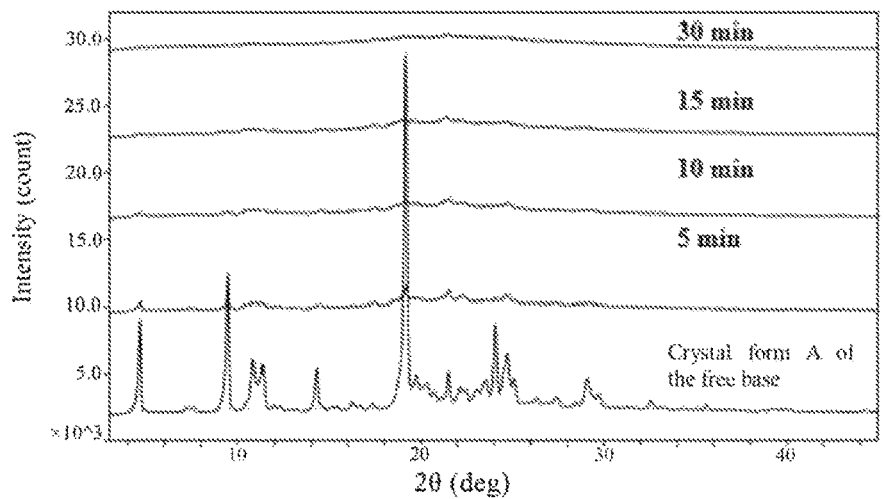
FIG. 27 is the XRPD pattern for the grinding stability of crystalline form A of the free base.
Figure 28:
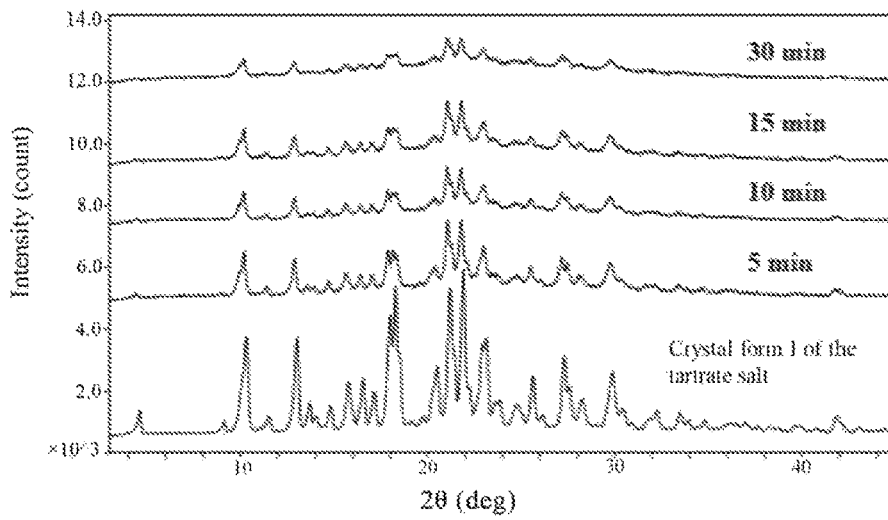
FIG. 28 is the XRPD pattern for the grinding stability of crystalline form I of the tartrate salt.
Figure 29:
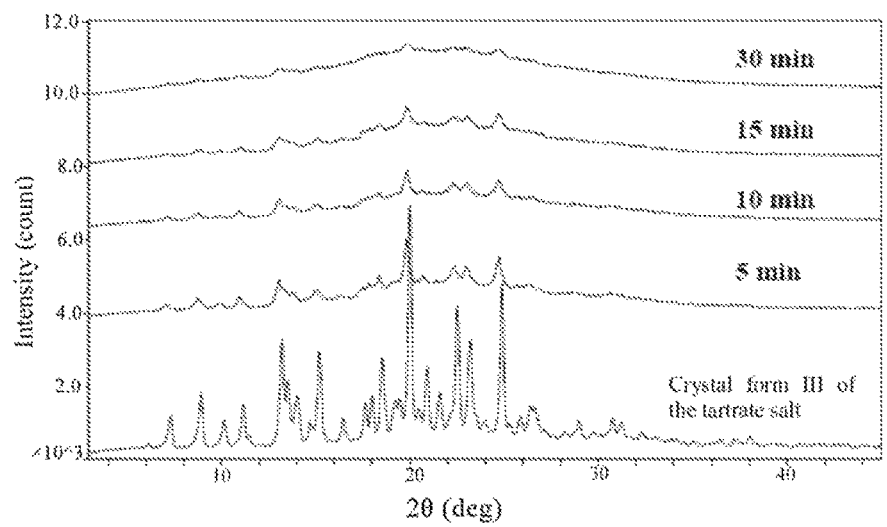
FIG. 29 is the XRPD pattern for the grinding stability of crystalline form III of the tartrate salt.

An appropriate amount of powders of crystalline form A of the free base, crystalline form I of the tartrate salt and crystalline form III of the tartrate salt were weighed and evenly spread in an agate mortar. Agate beads were added. To simulate the grinding conditions in a formulation process, the vibration frequency of the automatic ball mill was set at 25S-1, and the grinding was carried out for 5, 10, 15, and 30 min, respectively. Then samples were taken for XRPD to investigate the stability of the crystalline form under grinding conditions. For details of patterns, see FIGS. 27-29.

Comparison of XRPD results shows that crystalline form A of the free base and crystalline form III of the tartrate salt become amorphous under grinding conditions, while crystalline form I of the tartrate salt is only reduced in the degree of crystallinity. Therefore, crystalline form I of the tartrate salt is more stable under grinding conditions and thus more stable during formulation.

Example 9: Test of Water Adsorption and Desorption of the Tartrate Salt of the Compound of Formula (I)

Figure 4D:
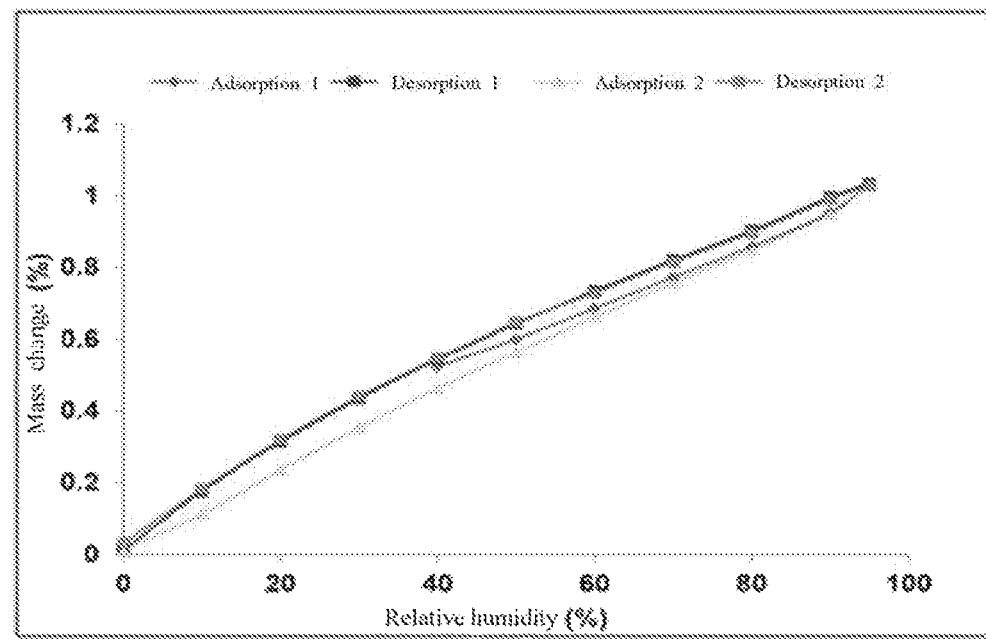
FIG. 4d shows the dynamic vapor sorption (DVS) isotherm plot of crystalline form I of tartrate salt of the compound of formula (I).
Figure 5:
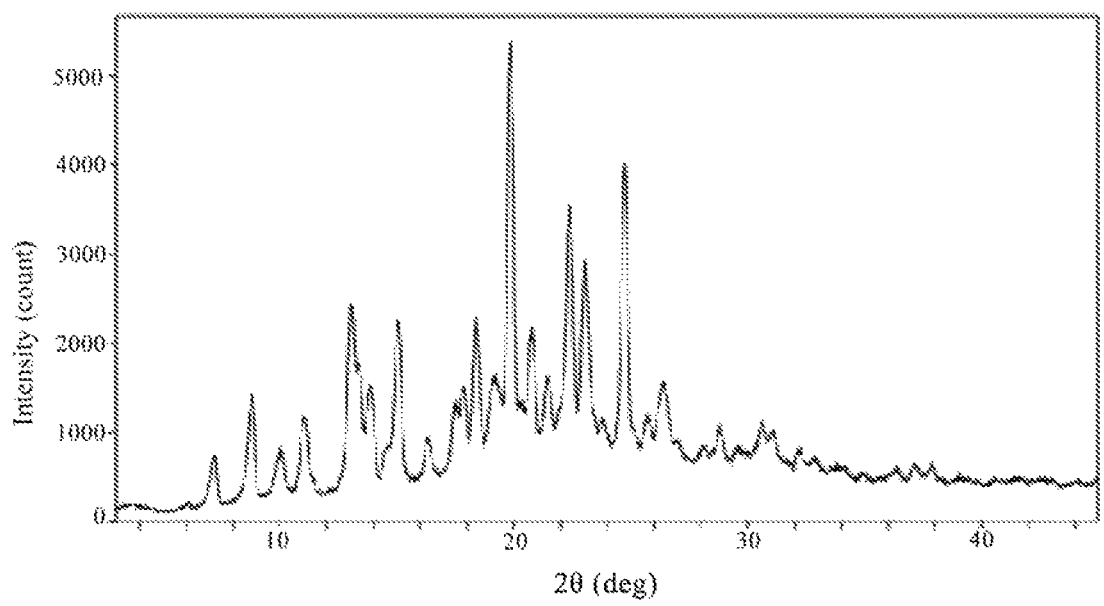
FIG. 5 is the X-ray powder diffraction (XRPD) pattern of crystalline form III of tartrate salt of the compound of formula (I).
Figure 5A:
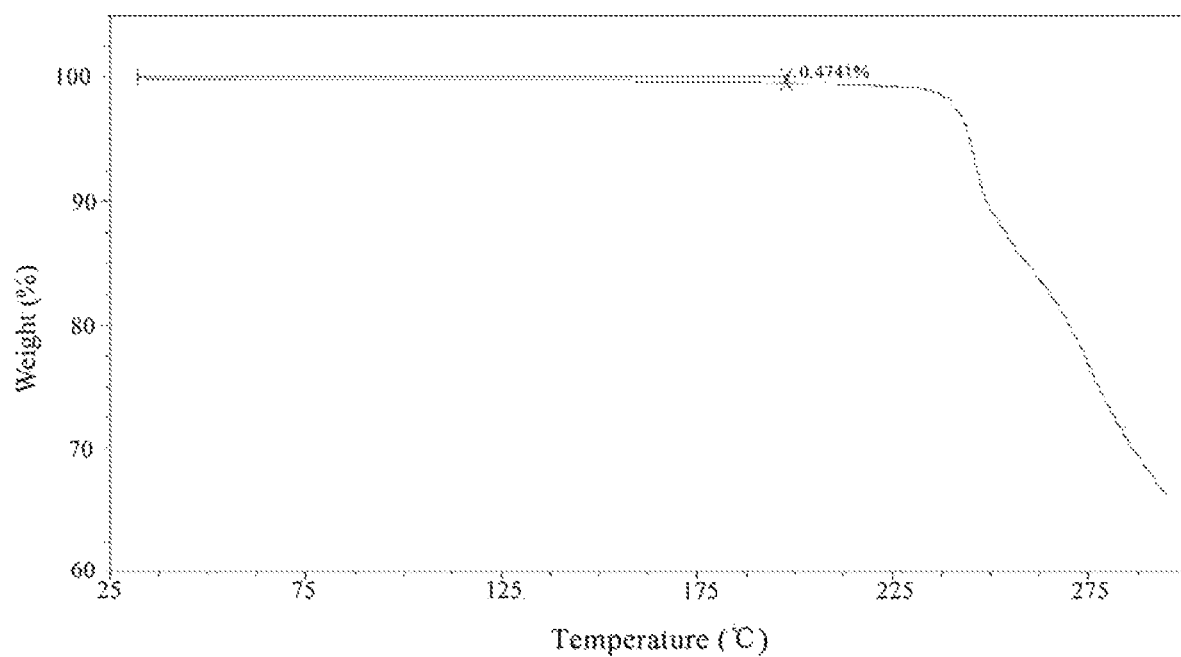
FIG. 5a shows the thermogravimetry analysis (TGA) of crystalline form III of tartrate salt of the compound of formula (I)
Figure 5B:
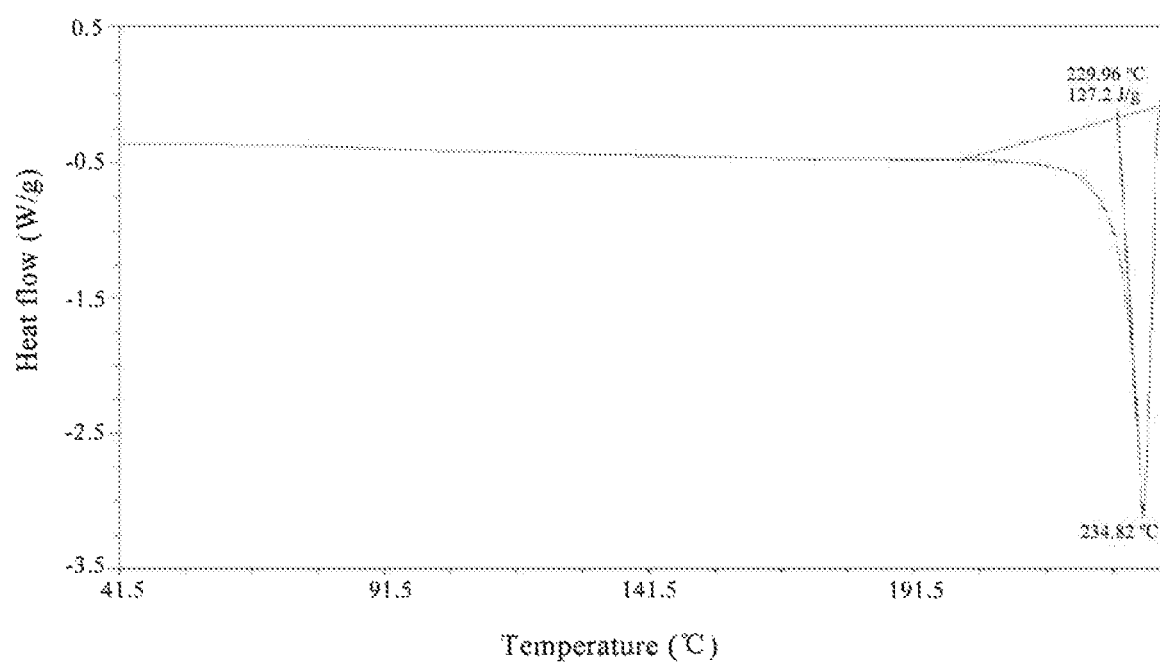
FIG. 5b shows the differential scanning calorimetry (DSC) analysis results of crystalline form III of tartrate salt of the compound of formula (I)
Figure 5C:
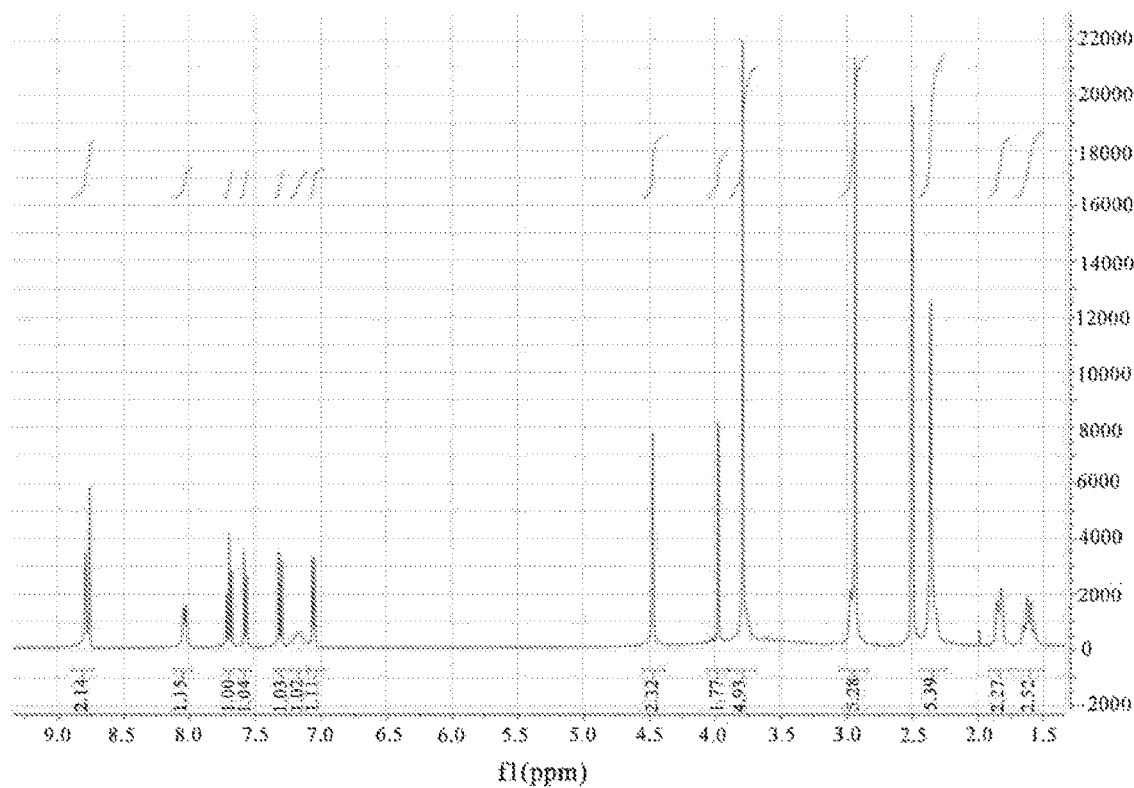
FIG. 5c shows the $^1$H NMR (DMSO-$d_6$) of crystalline form III of tartrate salt of the compound of formula (I)
Figure 5D:
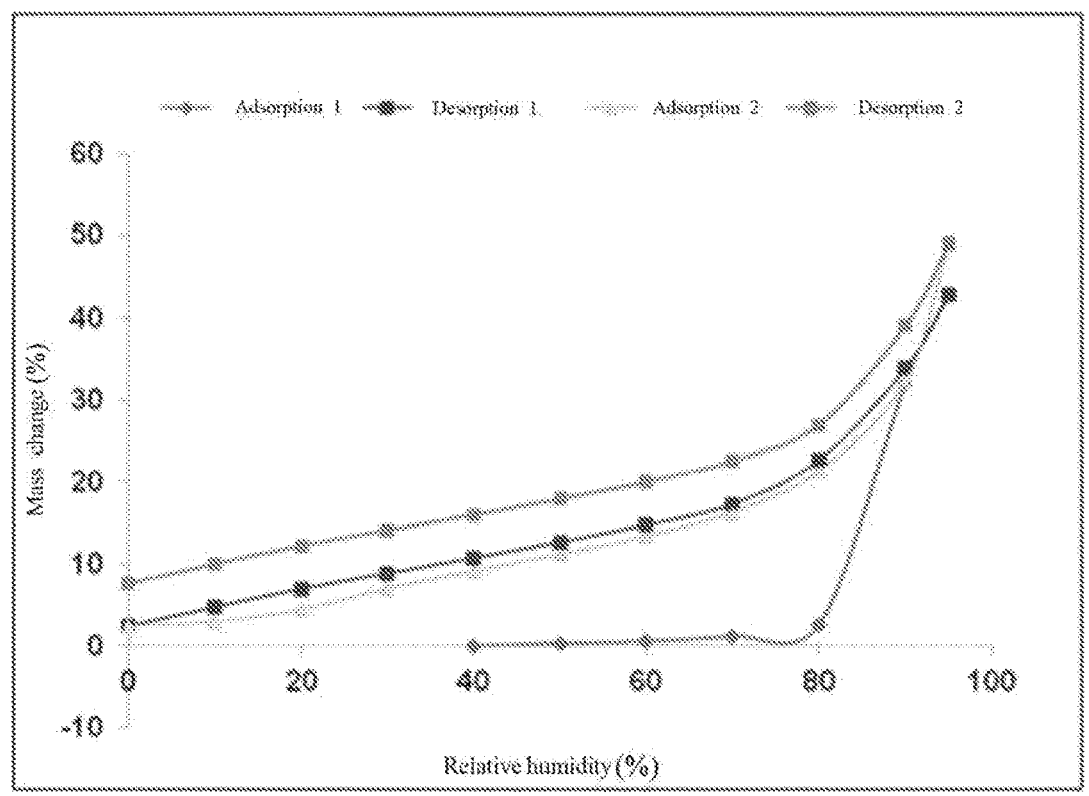
FIG. 5d shows the dynamic vapor sorption (DVS) isotherm plot of crystalline form III of tartrate salt of the compound of formula (I).

Dynamic water adsorption instrument (DVS) was used to investigate the adsorption and desorption test of crystalline forms I and III of the tartrate salt at 25° C. in the range of 0-95% relative humidity, so as to determine hygroscopicity of various crystalline forms (For details, see FIGS. 4d and 5d). The results show that in the humidity range of 40-80% RH, the moisture absorption of crystalline form I is 0.33%, and the moisture absorption of crystalline form III is 0.37%. Crystalline form I is significantly more stable than crystalline form III under high humidity conditions (RH >90%). Crystalline form III has a moisture absorption of 18.1% from 90% to 95% RH, while crystalline form I of the tartrate salt has almost no moisture absorption (0.08%).

Example 10: Study on the Transformation Relationship of the Tartrate Salt of the Compound of Formula (I)

Figure 30:
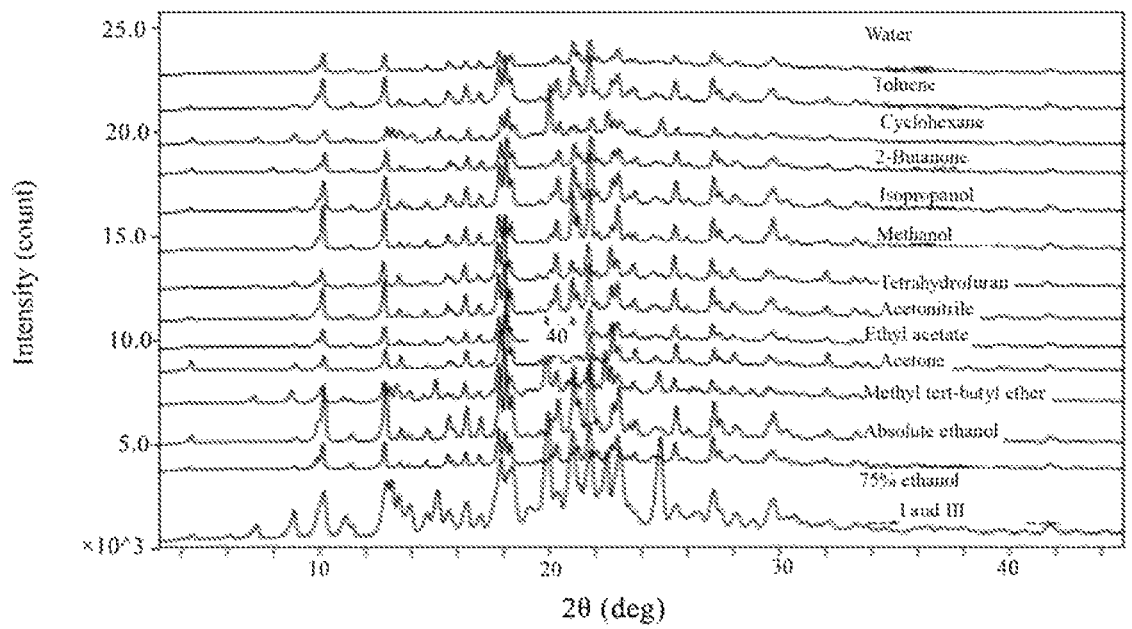
FIG. 30 is the analysis of the suspension competition assay of tartrate salt I and tartrate salt III at room temperature.
Figure 31:
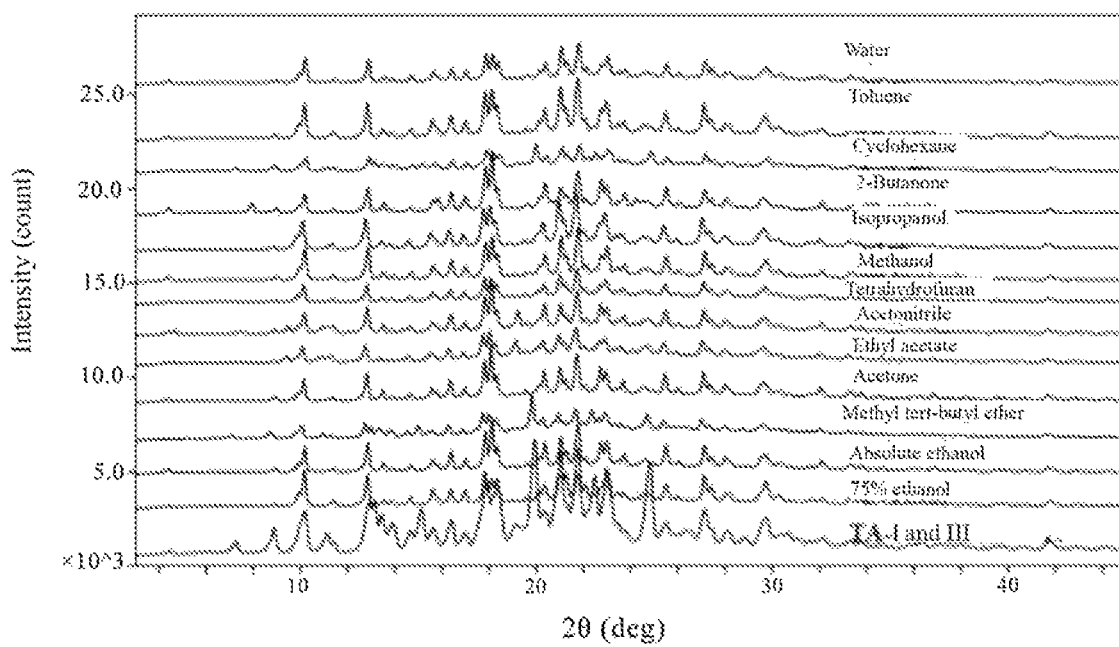
FIG. 31 is the analysis of the suspension competition assay of tartrate salt I and tartrate salt III at 50° C.

Suspension competitive crystal transformation studies were conducted on crystalline form I and crystalline form III in different organic solvents to determine stable crystalline forms under different conditions and determine the mutual transformation relationship between crystalline form I and crystalline form III. Crystalline form I and crystalline form III (each 20 mg) were weighed and added into a 2 mL or 10 mL glass bottle, and 0.5 mL or 1 mL of organic solvent was added, respectively, according to the solubility. Two batches were prepared with the same solvent, and placed respectively at room temperature and 50° C. for suspension competition for 24 h. The suspension was centrifuged (10000 rpm, 3 min). The obtained solid powder was then vacuum-dried and tested for XRPD (See FIGS. 30 and 31 for details). The results of the suspension crystal transformation test are shown in Table 2. The results show that, except methyl tert-butyl ether and cyclohexane, the physical mixture of crystalline form I and crystalline form III was transformed into crystalline form I after suspension competition in conventional solvents such as 75% ethanol, absolute ethanol, acetone, ethyl acetate, acetonitrile, tetrahydrofuran, methanol, isopropanol, 2-butanone, toluene, and water at room temperature and 50° ° C. It can be determined that crystalline form I is a stable crystalline form under these conditions.

TABLE 5

Results of the suspension crystal transformation test of crystalline forms I and III of tartrate salt of the compound of formula (I)

| No. | Reagent | Room temperature | 50° C. |
|---|---|---|---|
| 1 | 75% ethanol | I | I |
| 2 | Absolute ethanol | I | I |
| 3 | Methyl tert-butyl ether | Mixture | Mixture |
| 4 | Acetone | I | I |
| 5 | Ethyl acetate | I | I |
| 6 | Acetonitrile | I | I |
| 7 | Tetrahydrofuran | I | I |
| 8 | Methanol | I | I |
| 9 | Isopropanol | I | I |
| 10 | 2-Butanone | I | I |
| 11 | Cyclohexane | Mixture | Mixture |
| 12 | Toluene | I | I |
| 13 | Water | I | I |

To sum up, through the stability evaluation and solubility study of crystalline forms I and III of the tartrate salt, the crystalline form of the tartrate salt suitable for development was further screened out. The results of the stability test show that the solvent-mediated crystal transformation, grinding, and hygroscopic stability of crystalline form I were all better than those of crystalline form III.

The contents of all references (including literature references, issued patents, published patent applications and co-pending patent applications) cited in this application are hereby expressly incorporated by reference in their entirety. Unless defined otherwise, all technical and scientific terms used herein have the same meaning as commonly known to those skilled in the art.

All features disclosed in this specification may be combined in any combination. Each feature disclosed in this specification may be replaced by alternative features serving the same, equivalent or similar purpose. Thus, unless expressly stated otherwise, each feature disclosed is only example of a series of equivalent or similar features.

From the above description, those skilled in the art can easily ascertain the essential characteristics of the present invention, and without departing from the spirit and scope of the present invention, they can make various changes and modifications to the present invention to adapt it to various usages and conditions. Accordingly, other implementations are also within the scope of the claims.

What is claimed is:

1. A crystalline form A of a compound of formula (I):

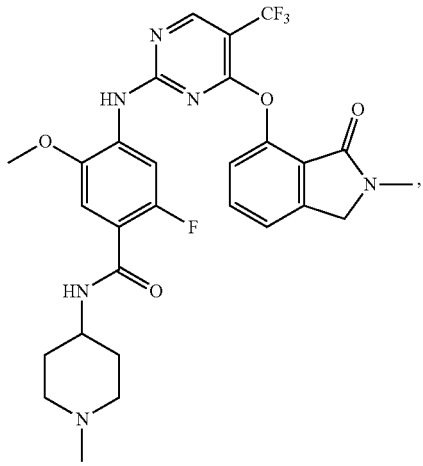

(I)

which is a free base of the compound of formula (I), characterized by an X-ray powder diffraction (XRPD) pattern comprising peaks at 10.979, 19.26, 21.581 and 24.801 degrees 2θ.

2. A crystalline form I of a salt of a compound of formula (I):

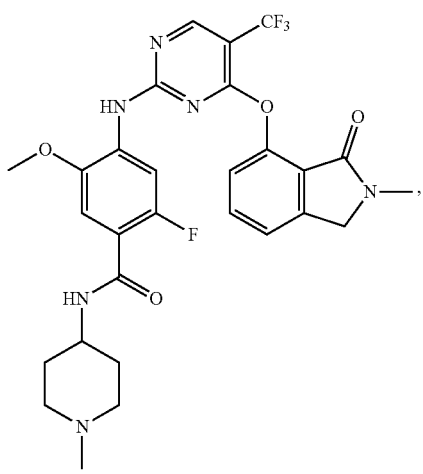

(I)

which is a tartrate salt of the compound of formula (I), characterized by an X-ray powder diffraction (XRPD) pattern comprising peaks at 10.34, 17.981, 18.281 and 21.901 degrees 2θ.

3. A pharmaceutical composition, comprising the crystalline form A of claim 1.

4. A pharmaceutical composition, comprising the crystalline form I of claim 2.

5. The crystalline form A of claim 1, wherein the X-ray powder diffraction (XRPD) pattern further comprises peaks at 4.781 and 22.26 degrees 2θ.

6. The crystalline form A of claim 5, wherein the X-ray powder diffraction (XRPD) pattern further comprises peaks at 9.58, 11.459, 14.678, 17.402, 22.54, and 29.219 degrees 2θ.

7. The crystalline form A of claim 6, wherein the X-ray powder diffraction (XRPD) pattern further comprises peaks at 7.361, 7.619, 10.54, 12.34, 12.96, 13.278, 18.54, 19.918, 23.521, 24.217, and 25.181 degrees 2θ.

8. The crystalline form A of claim 1, wherein the X-ray powder diffraction (XRPD) pattern further comprises peaks at 4.781, 5.255, 6.395, 7.361, 7.619, and 9.58 degrees 2θ.

9. The crystalline form I of claim 2, wherein the X-ray powder diffraction (XRPD) pattern further comprises peaks at 4.627 and 23.121 degrees 2θ.

10. The crystalline form I of claim 9, wherein the X-ray powder diffraction (XRPD) pattern further comprises peaks at 13.019, 21.2, 27.299, 27.541 and 29.879 degrees 2θ.

11. The crystalline form I of claim 10, wherein the X-ray powder diffraction (XRPD) pattern further comprises peaks at 15.76, 16.54, 17.159, 20.538, 24.721, 25.659, 32.277, and 41.821 degrees 2θ.

12. The solid crystalline form I of claim 2, wherein the X-ray powder diffraction (XRPD) pattern further comprises peaks at 4.637 and 9.143 degrees 2θ.

* * * * *